United States Patent
Bibillo et al.

(10) Patent No.: US 11,542,541 B2
(45) Date of Patent: Jan. 3, 2023

(54) METHOD AND SYSTEM FOR SAMPLING MATERIAL FROM CELLS

(71) Applicant: Bio-Rad Laboratories, Inc., Hercules, CA (US)

(72) Inventors: Arkadiusz Bibillo, Walnut Creek, CA (US); Pranav Patel, Pleasanton, CA (US); Christopher Reggiardo, Castro Valley, CA (US); Jonathan Petersen, Sunnyvale, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 128 days.

(21) Appl. No.: 17/105,333

(22) Filed: Nov. 25, 2020

(65) Prior Publication Data

US 2021/0155975 A1  May 27, 2021

Related U.S. Application Data

(60) Provisional application No. 62/940,866, filed on Nov. 26, 2019.

(51) Int. Cl.
*C12Q 1/68* (2018.01)
*C12Q 1/6806* (2018.01)
(Continued)

(52) U.S. Cl.
CPC ....... *C12Q 1/6806* (2013.01); *C12N 15/1003* (2013.01); *C12Q 1/6853* (2013.01); *C12Q 1/6874* (2013.01)

(58) Field of Classification Search
CPC ...................................................... C12Q 1/68
(Continued)

(56) References Cited

U.S. PATENT DOCUMENTS 6,071,394 A    6/2000  Cheng et al.
6,280,590 B1   8/2001  Cheng et al.
(Continued)

FOREIGN PATENT DOCUMENTS

CN   1626673 A      6/2005
CN   107462621 A    12/2017

OTHER PUBLICATIONS

Morshed, Bashir I. et al., "Electrical Lysis: Dynamics Revisited and Advances in On-chip Operation" Critical Reviews™ in Biomedical Engineering 41.1, pp. 37-50 (2013).
(Continued)

*Primary Examiner* — Aaron A Priest
(74) *Attorney, Agent, or Firm* — Kolisch Hartwell, P.C.

(57) ABSTRACT

Methods, systems, and devices for sampling/isolating material from cells. An exemplary system may comprise a chip including an electrode array of sampling electrodes arranged along a surface of the chip. A cell-receiving area may be located adjacent the surface of the chip. The system also may comprise a tag array of tags supported by the chip and aligned with the electrode array. Each tag of the tag array may include an identifier that is unique to the tag within the tag array. Each tag may be configured to bind nucleic acids, or a capturing agent distinct from the tag may be aligned with each sampling electrode of the electrode array to capture a protein or other analyte of interest. The system further may comprise a control circuit configured to apply an individually controllable voltage to each sampling electrode of the electrode array and measure an electrical property of the sampling electrode.

13 Claims, 22 Drawing Sheets

(51) Int. Cl.
*C12N 15/10* (2006.01)
*C12Q 1/6853* (2018.01)
*C12Q 1/6874* (2018.01)

(58) Field of Classification Search
USPC ........................................................ 435/6.1
See application file for complete search history.

(56) References Cited

U.S. PATENT DOCUMENTS

| | | |
|---|---|---|
| 6,319,472 B1 | 11/2001 | Ackley et al. |
| 6,355,491 B1 | 3/2002 | Zhou et al. |
| 6,682,936 B2 | 1/2004 | Kovacs |
| 6,716,642 B1 | 4/2004 | Wu et al. |
| 6,806,050 B2 | 10/2004 | Zhou et al. |
| 7,045,097 B2 | 5/2006 | Kovacs |
| 7,081,192 B1 | 7/2006 | Wang et al. |
| 7,101,717 B2 | 9/2006 | Kovacs |
| 7,425,308 B2 | 9/2008 | Ackley et al. |
| 7,955,842 B2 | 6/2011 | Lee et al. |
| 9,914,135 B2 | 3/2018 | Manaresi et al. |
| 10,640,824 B1* | 5/2020 | Peikon .............. G01N 27/44791 |
| 2005/0112544 A1* | 5/2005 | Xu .......................... C12M 41/36 435/287.1 |
| 2012/0225424 A1* | 9/2012 | Abassi ................... C12N 15/87 435/5 |
| 2019/0143340 A1 | 5/2019 | Manaresi et al. |
| 2020/0277663 A1* | 9/2020 | Ramachandran Iyer .................... C12Q 1/6881 |

OTHER PUBLICATIONS

Rodriques, Samuel G., et al. "Slide-seq: A scalable technology for measuring genome-wide expression at high spatial resolution" Science 363.6434, pp. 1463-1467 (2019).

Vickovic, S., et al. "High-density spatial transcriptomics arrays for in situ tissue profiling" bioRxiv (published online at dx.doi.org/10.1101/563338 on Feb. 28, 2019).

* cited by examiner

METHOD AND SYSTEM FOR SAMPLING MATERIAL FROM CELLS

CROSS-REFERENCE TO PRIORITY APPLICATION

This application is based upon and claims the benefit under 35 U.S.C. § 119(e) of U.S. Provisional Patent Application Ser. No. 62/940,866, filed Nov. 26, 2019, which is incorporated herein by reference in its entirety for all purposes.

INTRODUCTION

The transcriptome is the complete set of RNA transcripts, and the quantity of each RNA transcript, present in a cell and/or expressed from a genome under specific conditions and/or at a particular developmental stage. The study of the transcriptome is called transcriptomics and is concerned not just with cataloging RNA transcripts for a given cell but also quantifying changing expression levels in response to hormones, drugs, environmental factors, differentiation, development, or the like.

RNA sequencing provides a high-throughput approach to catalog the transcriptome of a cell. In this approach, RNA from a cell serves as a template for synthesis of complementary DNA (cDNA). The cDNA is then prepared for sequencing, such as by ligation to linkers and amplification.

Spatial transcriptomics is the study of the transcriptome of a genome in two or more dimensions, such as across a section of tissue. A technique for parallel acquisition of two-dimensional (2D) RNA sequencing information has been developed. In the technique, a tissue section is laid upon a slide carrying an arrangement of beads. RNA released from cells of the tissue section diffuses to the beads and serves as a template for synthesis of distinguishably tagged cDNA at each bead. Tagged cDNAs from different beads then are pooled and sequenced. cDNAs having the same tag are assumed to represent RNA molecules that originated from the same region or cell of the tissue section. However, the technique produces libraries of variable quality and complexity. New methods and systems for sampling nucleic acids from cells for sequencing, such as 2D RNA sequencing, are needed.

SUMMARY

The present disclosure provides methods, systems, and devices for sampling/isolating material, such as nucleic acids or a particular protein, from cells. An exemplary system may comprise a chip including an electrode array of sampling electrodes arranged along a surface of the chip. A cell-receiving area may be located adjacent the surface of the chip. The system also may comprise a tag array of tags supported by the chip and aligned with the electrode array. Each tag of the tag array may include an identifier that is unique to the tag within the tag array. Each tag may be configured to bind nucleic acids, or a capturing agent distinct from the tag may be aligned with each sampling electrode of the electrode array to capture a protein or other analyte of interest. The system further may comprise a control circuit configured to apply an individually controllable voltage to each sampling electrode of the electrode array and measure an electrical property of the sampling electrode.

DETAILED DESCRIPTION

Figure 1:
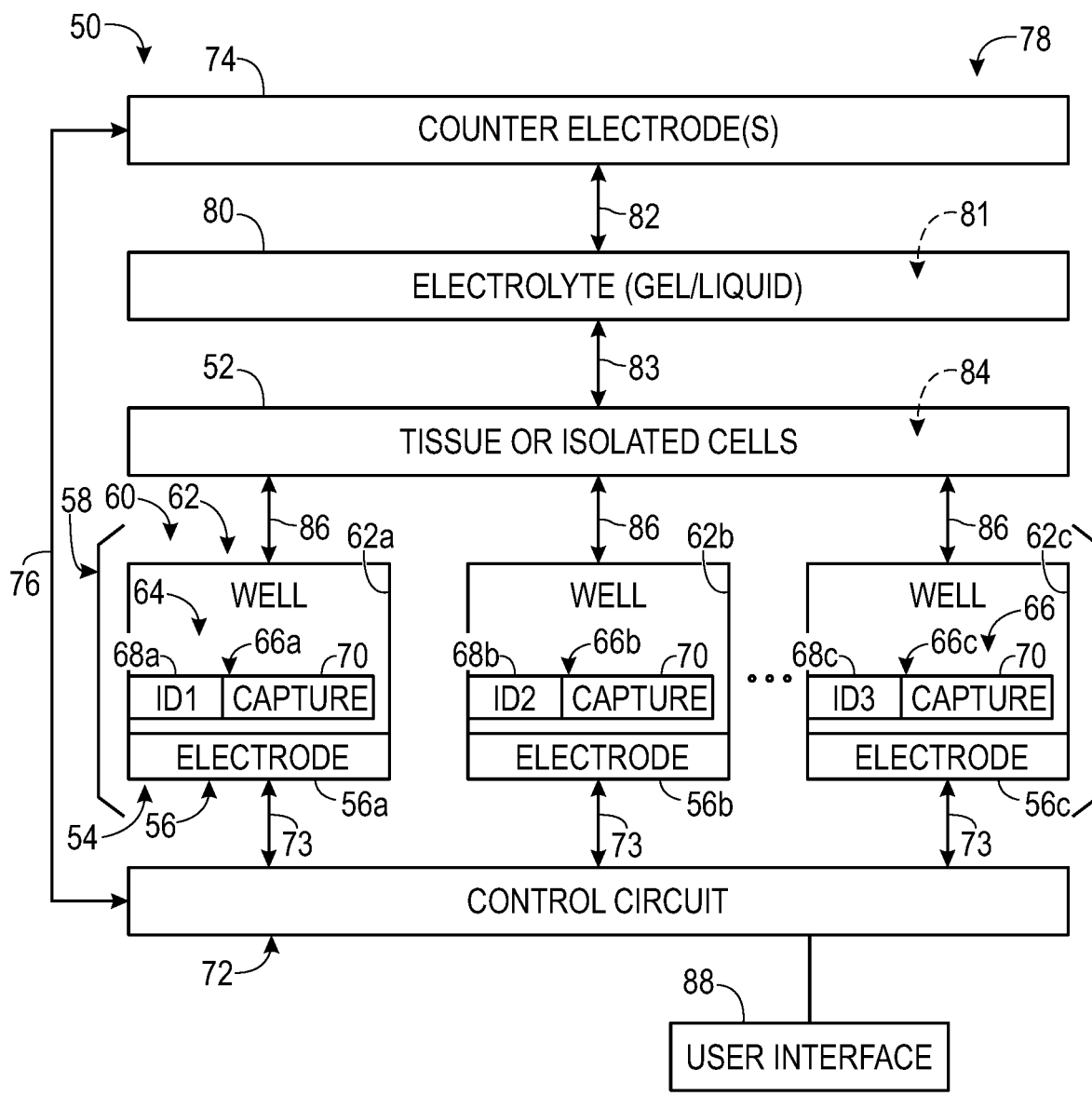
FIG. 1 is a block diagram of an exemplary system for sampling material from cells using an array of sampling electrodes.

The present disclosure provides methods, systems, and devices for sampling/isolating material (e.g., nucleic acids, such as RNA, or a protein or other analyte) from cells. An exemplary system may comprise a chip including an electrode array of sampling electrodes arranged along a surface of the chip, and optionally located at the bottom of a corresponding array of wells. A cell-receiving area may be located adjacent the surface of the chip. In some examples, the cell-receiving area may be configured to receive a tissue section including cells. The system also may comprise a tag array composed of tags, such as primers, supported by the chip and aligned with the electrode array. Each tag of the tag array may include an identifier that is unique to the tag relative to each other tag of the tag array. Each tag may be configured to bind nucleic acids, or a capturing agent distinct from the tag may be aligned with each sampling electrode of the electrode array to capture a protein or other analyte of interest. For example, each tag may be configured to hybridize with a poly(A) tail of messenger RNA molecules. The system further may comprise a control circuit configured to apply an individually controllable voltage to each sampling electrode of the electrode array and measure an electrical property of the sampling electrode. In some examples, the control circuit may be configured to apply a lysis voltage to the sampling electrode if the electrical property measured for the sampling electrode meets one or more criteria.

An exemplary method of sampling material from cells is disclosed. In the method, a plurality of cells may be received on a surface of a chip. The chip may include an electrode array of sampling electrodes arranged along the surface. An electrical property may be measured for each sampling electrode of the electrode array. A lysis voltage may be applied to the sampling electrode if the measured electrical property for the sampling electrode meets one or more criteria. An electrophoresis voltage may be applied to the sampling electrode, if the lysis voltage was applied to the sampling electrode, to drive nucleic acids (or other cell material of interest, such as a particular protein or other analyte), if any, that were released from one of the cells by applying the lysis voltage, toward the sampling electrode.

An exemplary method of sampling nucleic acid material from a tissue section is disclosed. In the method, a chip may be selected. The chip may include an electrode array of sampling electrodes arranged along a surface of the chip. The chip may support a primer array aligned with the electrode array. The primer array may be composed of primers, with each primer being configured to hybridize to a poly(A) tail of RNA and including an identifier that is unique to the primer within the primer array. The tissue section may be received on the surface of the chip. An electrical property may be measured for each sampling electrode of the electrode array. A lysis voltage may be applied to the sampling electrode if the measured electrical property for the sampling electrode meets one or more criteria. RNA molecules from the tissue section may be captured with each primer of a plurality of different primers of the primer array.

The present disclosure offers various improvements and advantages for 2D RNA sequencing to determine a 2D transcriptome profile of a tissue section, including any combination of the following. Known methods of preparing 2D RNA sequencing libraries rely on passive diffusion of RNA to beads carrying primers. However, RNA migration to the beads can be very inefficient, which causes inaccurate representation of RNA species, and the absence of rare RNA species, in the resulting library. In contrast, systems and methods of the present disclosure utilize electrophoresis to actively drive nucleic acids toward sampling electrodes. Actively driving nucleic acids facilitates capture and may result in a much higher yield of RNA captured by a respective primer located over each sampling electrode and much less lateral migration of RNA. In addition, known methods of preparing libraries for 2D RNA sequencing do not control release of RNA from individual cells of a tissue section. Instead, RNA is released from the tissue section by treating the entire tissue section with a reagent(s) to effect chemical lysis. As a result, RNA from different cells can migrate to the same bead, which destroys or at least degrades single-cell resolution of the resulting library. In contrast, systems and methods of the present disclosure use sampling electrodes to actively rupture membranes of cells by electrical lysis. This electrical lysis can be controlled electronically, to precisely control when and where lysis occurs across a tissue section, in some cases at a single-cell resolution. Moreover, this electrical lysis can be followed by electrophoresis to actively drive released nucleic acids to a primer or other capturing agent located over a sampling electrode. Accordingly, RNA can be controllably released with precision from selected cells of the tissue section in a spatially restricted manner and driven toward an aligned sampling electrode. In combination, these procedures may produce more efficient capture of RNA, and less lateral migration of RNA and mis-tagging of cDNA that degrades the quality of the resulting library. Furthermore, known methods of preparing libraries for 2D RNA sequencing do not provide any assessment of RNA release or capture, or library quality, without going through all the trouble and expense of preparing a library and acquiring sequence data from the library. In contrast, methods and systems of the present disclosure can predict, optionally in real time, where RNA has been captured with respect to an electrode array of sampling electrodes. The prediction may be based on electrical measurements and/or application of a lysis potential and/or an electrophoresis potential to particular sampling electrodes.

The methods and systems may utilize or include a chip having an array of wells that are aligned with an array of sampling electrodes. Each sampling electrode may be located at the bottom of a different well. The diameter of each well can be smaller or larger than the diameter of cells that are disposed on the chip. Accordingly, each well can receive nucleic acids from a single cell of a tissue section, if the diameter of the well is smaller than the diameter of the cells, or from multiple cells of a tissue section, if the diameter of the well is larger than the diameter of the cells. The presence of wells can offer various benefits. First, wells allow sampling electrodes, tags, capturing agents, and/or the like, to be located in and/or at the bottom of the wells, with an offset below the mouth of the well. With this offset, the lip of each well can be formed of a dielectric material. When a cell(s) covers the mouth of the well and moves into very close proximity or contact with the lip of well, the cell may be advantageously positioned for electrical lysis. Electric current may be forced to flow in a narrow gap, if any, between the cell and the lip of the well, because the cell's membrane and the lip are electrically insulating. This results in a high current density at the cell's membrane when a lysis voltage is applied, which can rupture the cell. Moreover, the positioning of a cell over the mouth of the well and very close to the well's lip can be detected as an increase in resistance to current flow between a sampling electrode at the bottom of the well and a counter electrode. Accordingly, by measuring an electrical property of the sampling electrode that reflects the resistance, an optimal timing for electrical lysis and a prediction of the success of the electrical lysis can be determined. Using this approach, the methods and systems can intelligently apply a lysis voltage followed by an electrophoresis voltage and an optional reverse voltage, to selected sampling electrodes.

The electronic component of the method and system provides advantages. First, rupturing a cell membrane electrically facilitates RNA capture. Second, the ability to predict where cells have been lysed offers a real-time assessment of the efficiency and location of captured nucleic acids. This information allows a user to evaluate the prospective two-dimensional quality of a library before it is constructed or used for sequencing. Recording the activities of sampling electrodes allows real-time display or post-sampling construction of a saturation map (i.e., a map of the sampling electrodes showing where RNA capture is predicted to have occurred). The saturation map allows the user to make knowledge-based decisions about the next steps, for example, whether to proceed with sequencing (e.g., based on quality, tissue surface coverage, etc.). Third, if a respective well is aligned with each sampling electrode, electric potential applied to the sampling electrode quickly dissipates lateral to the top of the well, which allows precise/specific collection of RNA from a cell(s) aligned with the well. Fourth, the method and system may use or include a chip having an integrated circuit (digital) connected to sampling electrodes (analog), where the sampling electrodes are positioned for contact with an electrolyte placed on the chip. The chip may, for example, have 1,000 to 100,000 sampling electrodes. Each sampling electrode may be located in a separate well, which may, for example, be 1-70 micrometers in diameter and 1-70 micrometers deep. Each well may contain a primer unique to that well, relative to each other well, and configured to capture RNA. The primer may include a unique identifier, such as a barcode sequence. Each electrode can be controlled individually and may measure a current/potential, which may be recorded for further analysis.

Further aspects of the present disclosure are described in the following sections: (I) definitions, (II) system, device, and method overview, (III) examples, and (IV) selected aspects.

I. DEFINITIONS

Technical terms used in this disclosure have meanings that are commonly recognized by those skilled in the art. However, the following terms may be further defined as follows.

Aligned—arranged along or centered on the same axis, such as an axis orthogonal to a planar surface/side of a chip or a central axis of a well of the chip.

Array—an arrangement of related elements (e.g., sampling electrodes, wells, tags, primers, identifiers, etc.), optionally a systematic arrangement, such as in rows and/or columns. The arrangement may include any suitable number of the elements, such as at least 10, 100, 1,000, 10,000, or 100,000, among others. An array may be an electrode array composed of an array of sampling electrodes, a well array composed of an array of wells, a tag array composed of an array of structurally different tags (e.g., different primers), or the like. Any array disclosed herein may be a planar array having its elements arranged along a plane, such as a plane defined by a surface of a chip (e.g., a top side and/or planar side of the chip). Two or more different arrays, such as an electrode array and a well array, or an electrode array and a tag array, may be parallel to the same plane. Any array disclosed herein may be a subarray of a larger array of the same type of elements. For example, a chip may include an electrode array composed of 1,000 sampling electrodes, and the electrode array may be a subarray within a larger array of more than 1,000 sampling electrodes on the chip. Two arrays are aligned with one another if each element of one of the arrays is aligned with a different element of the other array.

Capturing agent—a molecule, molecular region, or molecular complex that is immobilized and binds nucleic acids, such as by hybridization (i.e., base pairing), and/or attaches nucleic acids to an immobilized tag. The capturing agent may be immobilized by connection to a chip or a bead, among others. A capturing agent may be provided by a tag (e.g., by a region of the tag including a series of nucleotides), a protein(s), or the like. A capturing agent provided by a tag also may be called a capturing sequence. In some examples, the capturing agent is a specific binding partner, such as an antibody, that binds to a protein or other analyte of interest to be captured from lysed cells.

Cell—the basic structural, functional, and biological unit of a living organism. Exemplary cells include stem cells, established cells (e.g., cell lines), primary cells, cells of a tissue, transfected cells, cells from a clinical sample (e.g., a blood sample, a fluid aspirate, a tissue section, etc.), and/or the like. The cells of the present disclosure may be tissue cells or isolated cells, among others. The term "isolated cells" refers to single cells and/or clusters of cells that are not connected to one another.

Chip—an article including an integrated circuit. A chip may be referred to as being flat or a plate, which means that the chip has a length and width that are much greater than the chip's thickness, such as at least ten times the thickness. The chip may include a substrate, which is a layer or substratum below one or more other layers of the chip. The substrate may be formed of a semiconductor, such as silicon, gallium arsenide, gallium nitride, silicon carbide, or the like. The chip has a "top side" that can be oriented parallel to a horizontal plane and facing up, whether or not the chip is used for sampling nucleic acids in this orientation. The chip, and particularly the top side thereof, may have any suitable size and shape to match the size, shape, and/or type of target tissue/cells from which nucleic acids will be sampled.

Complementary—related by the rules of base pairing. A first nucleic acid, or region thereof, is "complementary" to a second nucleic acid if the first nucleic acid or region is capable of hybridizing with the second nucleic acid in an antiparallel fashion by forming a consecutive or nearly consecutive (uninterrupted) series of base pairs. The first nucleic acid (or region thereof) is termed "perfectly complementary" to the second nucleic acid if hybridization of the first nucleic acid (or region thereof) to the second nucleic acid forms a consecutive series of base pairs using every nucleotide of the first nucleic acid or region thereof. A "complement" of a first nucleic acid is a second nucleic acid that is perfectly complementary to the first nucleic acid for at least ten consecutive nucleotides. The "complementarity" between a first nucleic acid (or region thereof) and a second nucleic acid (or region thereof) refers to the number or percentage of base pairs that can be formed when the first nucleic acid (or region thereof) is optimally aligned for hybridization in an antiparallel fashion with the second nucleic acid (or region thereof). A first nucleic acid or region thereof that is complementary to a second nucleic acid or region thereof generally has a complementarity of at least 80% or 90%.

Control circuit—electronic circuitry configured to control and sense electrical properties of electrodes and including any number of digital and analog circuits, and optionally including a processor to perform operations on a data stream. A control circuit may be configured to communicate with a user and to output data reporting the current status or final results of a sampling run performed with the systems and devices of the present disclosure.

Degenerate—having a mix of sequences or nucleotide identities. A "degenerate primer" or a "degenerate tag" refers to a mix of primer oligonucleotides or tag oligonucleotides of related but not identical sequence. The aligned sequences of the primer oligonucleotides or tag oligonucleotides collectively define a "consensus sequence" for the degenerate primer or degenerate tag, which indicates the identity of the single nucleotide, or two or more different nucleotides, present at each nucleotide position along the degenerate primer or tag. The degeneracy of the degenerate primer or tag refers to the number of different primer or tag oligonucleotide sequences constituting the degenerate primer or tag, and the degeneracy of a nucleotide position of the degenerate primer or tag indicates how many different nucleotides are present at that position in the mix. The degeneracy of a given nucleotide position of a degenerate primer or tag may be 1, 2, 3, or 4, among others. Each "N" in the consensus sequence of a degenerate primer or tag increases its degeneracy by a factor of four.

Electrode—a conductor for contacting an electrolyte. The conductor may be formed of any suitable electrically conductive material, such as a noble metal or a noble metal alloy (e.g., gold, platinum, rhodium, iridium, palladium, ruthenium, osmium, or a combination thereof). An electrode may, for example, be a sampling electrode, a guard electrode, or a counter electrode. The term "sampling electrode" refers to an electrode toward which nucleic acids are attracted, such as for capture and isolation. The term "guard electrode" refers to an electrode located intermediate two or more sampling electrodes and configured to increase electrical isolation of the sampling electrodes from one another. The term "counter electrode" refers to an electrode that can complete circuits with sampling electrodes and/or one or more guard electrodes and allows a voltage to be applied to the sampling electrodes and/or guard electrode(s). Accordingly, application of a voltage to an electrode, such as a sampling electrode, as used herein, means that the voltage is applied between the electrode and a counter electrode. The phrase "at a sampling electrode" means in close proximity to the sampling electrode, such as located in a well that is aligned with the sampling electrode, but not necessarily in contact with the sampling electrode. The phrase "at a sampling electrode" can mean located closest to the sampling electrode relative to each other sampling electrode of an electrode array, and/or within a distance of 50, 20, 10, or 5 micrometers of the sampling electrode.

Electrolyte—an electrically conductive medium including free ions in solution. An electrolyte may be a liquid (i.e., an electrolyte liquid) or a gel (i.e., an electrolyte gel). An exemplary electrolyte of the present disclosure includes an aqueous solution of free ions.

Lysis—disintegration of the membrane and/or wall of a cell(s). The verb "lyse" means undergoing or causing to undergo lysis.

Messenger RNA—RNA containing a poly(A) tail and/or that conveys genetic information to a ribosome.

Nucleic acid—a polymer of any length composed of naturally-occurring nucleotides (e.g., where the polymer is DNA or RNA), or a substance produced synthetically that can hybridize with DNA or RNA in a sequence-specific manner analogous to that of two naturally occurring nucleic acids, e.g., can participate in Watson-Crick base pairing interactions. A nucleic acid may be composed of any suitable number of nucleotides, such as at least about 5, 10, 100, or 1000, among others. Generally, the length of a nucleic acid corresponds to its source, with synthetic nucleic acids (e.g., oligonucleotides) typically being shorter, and biologically/enzymatically generated nucleic acids (e.g., genomic fragments) typically being longer.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (G)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone and/or to one or more nucleobases. Exemplary artificial nucleic acids include glycol nucleic acids (GNAs), peptide nucleic acids (PNAs), locked nucleic acids (LNAs), threose nucleic acids (TNAs), xeno nucleic acids (XNA), and the like.

The sequence of a nucleic acid is defined by the order in which nucleobases are arranged along the backbone. This sequence generally determines the ability of the nucleic acid to hybridize with another nucleic acid by hydrogen bonding. In particular, adenine pairs with thymine (or uracil) and guanine pairs with cytosine.

Oligonucleotide—a relatively short and/or chemically synthesized nucleic acid. The length of an oligonucleotide may, for example, be 3 to 1000 nucleotides, among others.

Primer—an oligonucleotide capable of serving as a point of initiation of template-directed nucleic acid synthesis under appropriate reaction conditions (e.g., in the presence of a template to which the primer hybridizes, nucleoside triphosphates, and an enzyme to catalyze polymerization (such as a DNA or RNA polymerase or a reverse transcriptase), in an appropriate buffer and at a suitable temperature). The primer may have any suitable length, such as 5 to 500 nucleotides, among others. The term "primer binding site" refers to a portion of a template to which a primer anneals. The full sequence of the primer need not be perfectly complementary to the primer binding site, just sufficiently complementary to anneal under the conditions of the reaction. Accordingly, the primer may have a 3'-end region that is complementary to the primer binding site, and a 5'-end region that is not complementary to the primer binding site.

Tag—an oligonucleotide including an identifier, which may be composed of any suitable number of nucleotides, such as at least 4, 5, 6, or more nucleotides. The identifier may be described as a unique molecular identifier or molecular barcode. A tag array may be composed of tags each including a different identifier that is unique within the tag array, that is, with respect each other tag of the tag array. The sequence of the different (unique) identifier present at each position of the tag array may be known, such that each identifier sequence represents a known spatial position within the array. Except for different identifier sequences, the sequences of the tags may be identical to one another otherwise. In some examples, each tag also may include a capturing agent that hybridizes to nucleic acids, such as messenger RNA molecules, via a capturing sequence of the tag. The capturing sequence may, for example, be configured to hybridize to the poly(A) tail of messenger RNA. In other examples, the capturing agent and the tag may be discrete relative to one another. The unique identifier sequence of each tag may be used, when analyzing sequence data from a resulting library, to identify the particular sampling electrode and/or well in the electrode array and/or well array from which each sequenced library member originated.

Template—a nucleic acid that serves as a pattern for synthesis of a complementary strand. The template may provide a primer binding site for a primer, which is extended by sequential addition of complementary nucleotides according to the pattern.

Tissue—an aggregate of cells from a multicellular organism or created in vitro. Tissue may, for example, form a structural material with one or more specific functions or represent abnormal growth (such as cancer). The term "tissue" includes a single type of tissue, such as muscle, nervous, connective, epithelial, tumor, or the like, or two or more types of tissue that are connected to one another to create a more complex structure, such as an organ or portion thereof. A "tissue section" refers to a slice of tissue. The tissue section may have any suitable thickness, such as less than (or greater than) about 100, 50, 20, or 10 micrometers, among others, and/or less than (or greater than) about 5, 3, or 2 times the average diameter of cells in the tissue section. The tissue section may be obtained from any suitable organ or tissue type, and may be prepared as a frozen section, a fixed section, a fresh section, and/or the like.

Well—a depression or recess of any suitable size and shape. The wells of a well array, as disclosed herein, may have a diameter of less than 100, 50, 25, 10, or 5 micrometers, and/or a diameter greater than 1, 2, or 5 micrometers, among others. The diameter may, for example, be 1-100, 1-70, or 1-50 micrometers, or the like. The wells may have a depth of less than 100, 50, 25, 10, or 5 micrometers, and/or a depth greater than 1, 2, or 5 micrometers, among others. The depth may, for example, be 1-100, 1-70, or 1-50 micrometers, or the like. The diameter of the wells may be greater than, less than, or about the same as the depth. Accordingly, the wells may be shallow recesses, deep holes, or something intermediate these extremes. Each well may have any suitable shape, such as cylindrical, conical, rectangular, or the like.

II. SYSTEM, DEVICE, AND METHOD OVERVIEW

Figure 2:
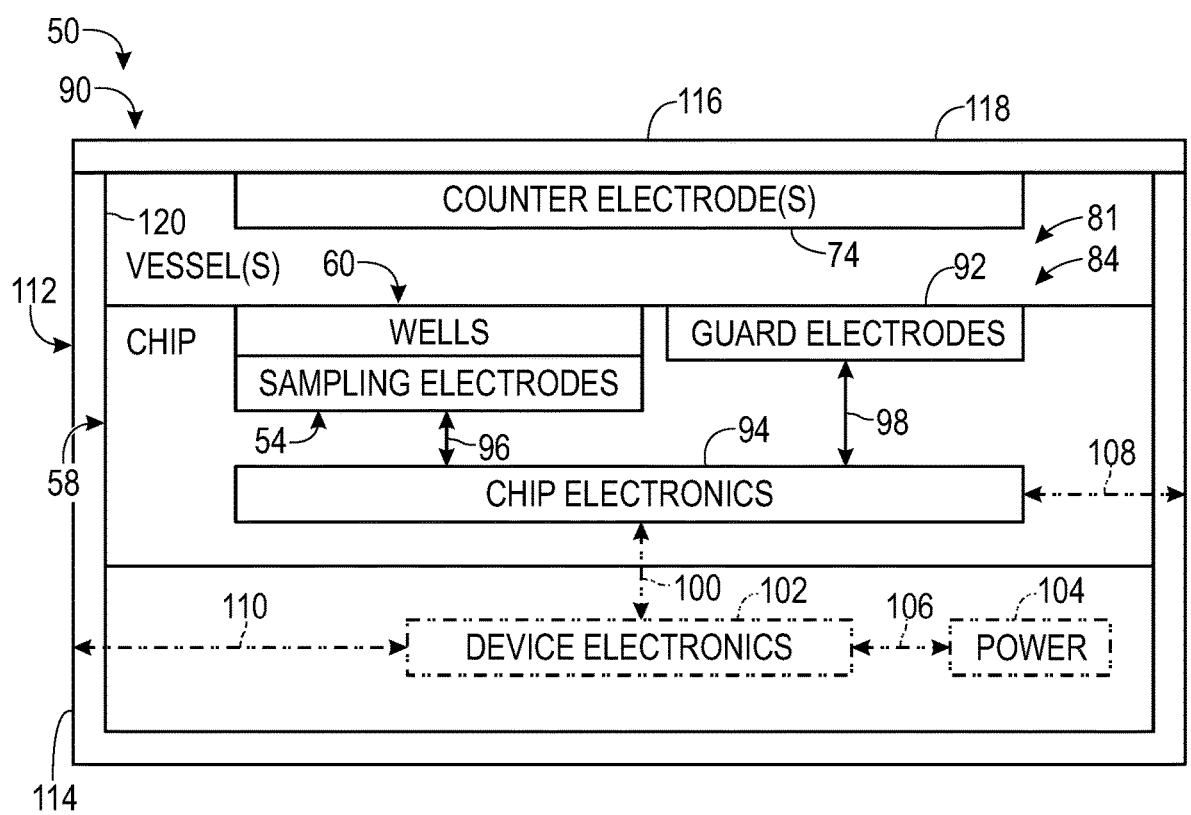
FIG. 2 is a schematic side view of an exemplary isolation device to provide the array of sampling electrodes for the system of FIG. 1.
Figure 3:
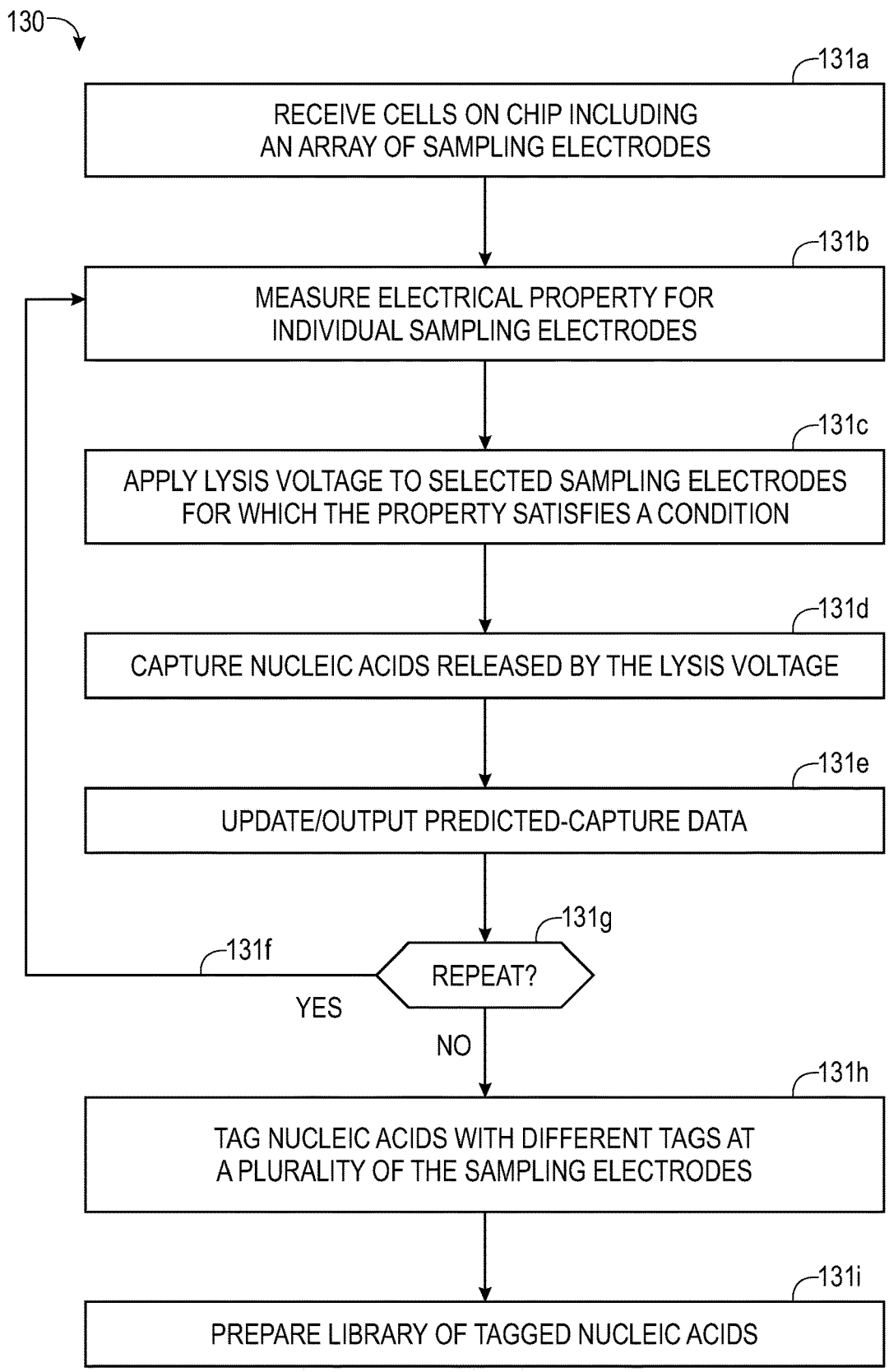
FIG. 3 is a flowchart listing exemplary steps that may be performed in an exemplary method of sampling material from cells using an array of sampling electrodes.

This section provides an overview of the sampling systems, devices, and methods disclosed herein; see FIGS. 1-3.

FIG. 1 shows an exemplary sampling system 50 for sampling nucleic acids from cells 52 using an electrode array 54 of sampling electrodes 56, which are provided by a chip 58. Only three illustrative sampling electrodes 56a, 56b, and 56c are shown in FIG. 1 for clarity. However, chip 58 may include any suitable number of sampling electrodes 56, such as at least 100 or 1,000 sampling electrodes, as indicated by an ellipsis between illustrative sampling electrodes 56b and 56c. Sampling system 50 is shown and described herein with electrode array 54 in a horizontal configuration and facing up, but electrode array 54 may be used in any suitable orientation.

Chip 58 may define a well array 60 aligned with electrode array 54. Well array 60 is composed of wells 62, including illustrative wells 62a, 62b, and 62c. Each sampling electrode 56, such as illustrative sampling electrodes 56a, 56b, and 56c, may be aligned with a different well 62 of well array 60, such as illustrative wells 62a, 62b, and 62c, respectively, and may be located in the different well, such as at the bottom thereof. Accordingly, the top surface of each sampling electrode 56 may be recessed with respect to a surrounding dielectric top surface of chip 58. In other examples, wells 62 may be omitted and the top surface of each sampling electrode 56 may be flush or elevated with respect to a dielectric top surface of the chip.

Chip 58 may support a tag array 64 of tags 66, including illustrative tags 66a, 66b, and 66c. Tags 66 each may have a different nucleotide sequence. Tag array 64 may be aligned with electrode array 54 and well array 60, with copies of a different tag 66 of tag array 64 located over each sampling electrode 56, such as vertically aligned with the electrode and the corresponding well. For example, in FIG. 1, illustrative tags 66a, 66b, and 66c are vertically aligned with illustrative electrodes 56a, 56b, and 56c, respectively, and vertically aligned with illustrative wells 62a, 62b, and 62c, respectively. Tags 66 may be located in corresponding wells 62 and may be primers.

Each tag 66 of tag array 64 may include a different identifier 68, such as illustrative identifiers 68a, 68b, and 68c (also called unique molecular identifiers (UMIs)). Tags 66 may differ in nucleotide sequence from one another only at identifiers 68, which may be created by subsequences in the tags. Each identifier ultimately may provide a record of the particular sampling electrode and/or well within the electrode array and/or well array from which each corresponding library member originated.

Copies of a capturing agent 70 may be aligned with each sampling electrode 56 and well 62. Capturing agent 70 may be provided by tags 66. For example, in FIG. 1, each of illustrative tags 66a, 66b, and 66c includes the same capturing agent 70, which may be formed by a distinct subsequence within each tag relative to identifiers 68a, 68b, and 68c.

Sampling system 50 may release cell material, such as nucleic acids, from individual cells 52 by electrical lysis. This lysis may be induced by energizing selected sampling electrodes 56 of electrode array 54 via a control circuit 72. The control circuit 72 may be in electrical contact with each sampling electrode 56, indicated at 73, and in electrical contact with one or more counter electrodes(s) 74, indicated at 76. Nucleic acids may be released from one or more cells of cells 52 that are located vertically above a given energized sampling electrode 56 and/or the corresponding well 62, and electrophoresed toward the given sampling electrode 56. Electrophoresis of the released nucleic acids may be driven by further energization of the given sampling electrode 56 via control circuit 72, to allow capture by copies of capturing agent 70 located over the given sampling electrode 56. The captured nucleic acids, or fragments thereof, may be tagged by the particular tag 66 located over the given sampling electrode 56, or may template the synthesis of complements of the captured nucleic acids, which may be tagged by the particular identifier 68, as explained further below.

Sampling system 50 includes an electrolytic assembly 78 formed by counter electrode(s) 74, an electrolyte 80 (gel and/or liquid), cells 52, electrode array 54, and control circuit 72. Electrolyte 80 may be located in an electrolyte-receiving space 81 adjacent counter electrode(s) 74 (also see FIG. 2). The electrolyte may be positioned under and in contact with counter electrode(s) 74, indicated at 82. Electrolyte 80 also may be located adjacent, indicated at 83, a cell-receiving area 84 for cells 52, which in turn may be adjacent a top surface of chip 58. Electrolyte 80 may be located under and over cells 52, with electrolyte 80 also present in wells 62.

Counter electrode(s) 74 is spaced from electrode array 54, optionally located vertically above electrode array 54, and provides a counter electrode for each sampling electrode 56 of electrode array 54. In some examples, counter electrode(s) 74 may be described as a top electrode(s). Counter electrode(s) 74 may, for example, be formed by a single conductive plate or a plurality of separate conductive plates. The horizontal area occupied by counter electrode(s) 74 may be at least as large as the horizontal extent (length times width) occupied collectively by electrode array 54, and/or each sampling electrode 56 may be vertically aligned with counter electrode(s) 74.

During operation of system 50, the electric potential of counter electrode(s) 74 may be held constant by control circuit 72, to provide an electric potential reference, while the electric potentials of sampling electrodes 56 are varied, to apply voltages individually to electrodes 56. Control circuit 72 may be configured to switchably and individually create a negative potential difference or a positive potential difference between any given sampling electrode 56 and counter electrode(s) 74. In other words, counter electrode(s) 74 can switch between serving as an anode (positive potential) and a cathode (negative potential) and with respect to any given sampling electrode 56.

Sample system 50 also may include a user interface 88 to permit a user to communicate with control circuit 72. User interface 88 may include any suitable combination of one or more input devices (e.g., a keyboard, a mouse, a keypad, a touch screen, and/or the like) and one or more output devices (e.g., a display, a touch screen, a printer, a speaker, and/or the like). The user interface may output data to the user during a sampling run (e.g., reported and updated in real time), and/or after the end of the sampling run. The data may report a number, a percentage, and/or a map of sampling electrodes 56 vertically over which cell lysis and/or capture of nucleic acids is predicted to have occurred.

FIG. 2 shows a schematic side view of an exemplary isolation device 90 to provide at least part of sampling system 50 of FIG. 1. Isolation device 90 includes chip 58 having electrode array 54 (of sampling electrodes) and well array 60 as described above. Chip 58 may or may not be removable from isolation device 90. In some examples, chip 58 may be disposable (single-use) and the rest of isolation device 90 may be reusable.

Chip 58 also may include one or more guard electrodes 92 that function to electrically isolate sampling electrodes 56 from one another. The horizontal position of guard electrode(s) 92 is not shown accurately in FIG. 2, as guard electrode(s) 92 is typically vertically aligned with the area bounded by a polygon circumscribing electrode array 54. See Example 2 for exemplary guard electrodes that may be suitable for chip 58.

Chip 58 further may include onboard chip electronics 94. Chip electronics 94 may include analog and/or digital circuitry. Each sampling electrode of electrode array 54 may be in electrical contact with chip electronics 94, indicated at 96. Each guard electrode 92 also may be in electrical contact with chip electronics 94, indicated at 98. (The horizontal/vertical positions of chip electronics 94 within chip 58 are not shown accurately here.)

Chip electronics 94 also may be in electrical contact, indicated at 100, with optional device electronics 102 that are separate from chip 58. Device electronics 102 may include analog and/or digital circuitry, and may have any suitable position in isolation device 90 relative to chip 58, such as below, above, or laterally offset from chip 58. An optional power supply 104, such as a battery, may supply electrical power, indicated at 106, to chip electronics 94 and device electronics 102, or off-device power (e.g., AC power from an electrical grid or an external battery) may be used as a power supply instead. Chip electronics 94 and device electronics 102 may form all of control circuit 72 of system 50 (also see FIG. 1). Alternatively, a portion of control circuit 72 may be formed by analog and/or digital circuitry that is separate from isolation device 90. Accordingly, chip electronics 94 and/or device electronics 102 may communicate with this external portion of control circuit 72, indicated respectively at 108 and 110, via respective communication ports formed by isolation device 90.

Isolation device 90 may include a housing 112 to support, enclose, and/or protect chip 58 and other device components. Housing 112 may have a base 114 and a cover 116 received on the base. Cover 116 may be completely removable or at least movable (e.g., pivotable or slidable) with respect to base 114. Counter electrode(s) 74 may be attached to an underside of a body 118 of cover 116.

Isolation device 90 may form at least one vessel 120 to hold cells 52 and electrolyte 80 (also see FIG. 1). Each vessel 120 may, for example, be a chamber, as depicted, including electrolyte-received space 81 and cell-receiving area 84 between chip 58 and counter electrode(s) 74. In other examples, each vessel may be a channel (e.g., see Example 6). At least a portion of the floor of the vessel may be provided by chip 58. Side walls of vessel 120 may be formed by housing 112, such as by base 114 thereof. At least a portion of the ceiling of vessel 120 may be formed by counter electrode(s) 74 and/or cover 116.

FIG. 3 is a flowchart listing exemplary steps that may be performed in a method 130 of sampling material, such as nucleic acids, from cells using an array of sampling electrodes. The steps listed in the flowchart of FIG. 3 may be performed in any suitable order and combination, and may be modified or supplemented as described elsewhere in the present disclosure, such as in Sections I, III, and IV.

Cells may be received on a chip including an array of sampling electrodes, indicated at 131*a*. A section of tissue including the cells may be received vertically above the electrode array, or isolated cells may be received vertically above the electrode array by flow of an electrolyte in which the cells are located (also see Examples 5 and 6).

An electrical property may be measured for individual sampling electrodes of the electrode array, indicated at 131*b*. The electrical property may be electric current, voltage, resistance, or the like. In some examples, a control circuit may apply a test voltage or a test current to individual sampling electrodes and measure the current or voltage resulting from the test voltage or current.

A lysis voltage may be applied to selected sampling electrodes for which the measured electrical property (e.g., electric current) satisfies at least one condition, indicated at 131*c*. For example, the lysis voltage for a given sampling electrode may be applied if one or more values or measurements for the measured electrical property of the given sampling electrode meet one or more criteria, which may be predefined before the sampling run begins. In some cases, a value for the measured electrical property of the given sampling electrode may be compared to a threshold, and the lysis voltage may be applied to the given sampling electrode if the value is less than (or greater than) the threshold.

The lysis voltage is applied between the given sampling electrode and the counter electrode. This voltage has a magnitude and duration designed to lyse one or more cells located vertically above the given sampling electrode and/or a corresponding well (and/or aligned with the sampling electrode and/or well). The lysis voltage may be applied as a single pulse, or two or more pulses, of elevated voltage for any suitable total duration or duration for each pulse, such as less than 10, 5, 2, or 1 second(s), among others. The lysis voltage may be elevated with respect to the test voltage applied in step 131*b*, such as at least 2, 3, 4, or 5 times the test voltage. Accordingly, application of the lysis voltage may be described as applying a voltage spike to the given sampling electrode. The lysis voltage may have a predefined profile (magnitude and duration) for the sampling run, where the profile is chosen according to the type of cells/tissue being investigated, how the cells and/or tissue is prepared, and/or the like.

Nucleic acids or other material released by step 131*c* may be captured, indicated at 131*d*. More specifically, an electrophoresis voltage may be applied to the given sampling electrode, after application of the lysis voltage. The electrophoresis voltage drives nucleic acids electrophoretically to a capturing agent located at the given sampling electrode and/or in the corresponding well, from one or more cells aligned with (e.g., located vertically above or on) the given sampling electrode and/or corresponding well. The electrophoresis voltage may (or may not) be less than the lysis voltage applied to the given sampling electrode, such as less than 50% or 30% of the lysis voltage. The electrophoresis voltage may be applied for any suitable amount of time, such as at least 1, 2, 5, or 10 seconds, and/or at least 2, 5, 10, or 20 times the duration of the lysis voltage, among others.

Capture of nucleic acids may be achieved by any suitable non-covalent molecular interactions, including hydrogen bonds, dipole-dipole interactions, and/or London dispersion forces, among others, and/or may be achieved by covalently bonding the nucleic acids, or fragments thereof, to the particular tag located at the given sampling electrode. In some examples, the nucleic acids may be RNA molecules including a poly(A) tail (i.e., messenger RNAs), and capture may result from hybridization of the poly(A) tail to a complementary sequence of the capturing agent. In some examples, capture may be result from interaction between DNA from a cell(s) and a DNA-binding agent, such as a DNA-binding protein. The DNA-binding agent may bind to DNA, such as double-stranded DNA, with or without sequence specificity. In some examples, capture may include covalently attaching nucleic acids to a tag that is immobilized at the given sampling electrode (e.g., see Example 7).

Predicted-capture data for the array of sampling electrodes may be updated and/or outputted, indicated at 131*e*. The capture data may be predicted based on application of the lysis voltage and/or electrophoretic voltage. For example, capture of nucleic acids may be predicted based on which sampling electrodes received the lysis voltage and/or the electrophoretic voltage. Alternatively, or in addition, capture may be predicted based on which sampling electrodes that received the lysis voltage exhibited at least a threshold change in the measured electrical property, when values of the electrical property are compared before and after application of the lysis voltage. For example, if electric current is the electrical property measured, sampling electrodes exhibiting at least a threshold increase in electric current in response to application of the lysis voltage may be predicted to have lysed and released nucleic acids that were captured by the capturing agent at the corresponding sampling electrodes. The predicted-capture data may represent a real time (or end of sampling run) estimate of the number, percentage, and/or locations at which cell lysis and capture of lysis-released nucleic acids are predicted to have occurred. Outputting the predicted-capture data may include displaying the capture data (with a display device) and/or printing the capture data with a printer.

Method 130 may return to step 131*b*, indicated at 131*f*, any suitable number of times for each sampling electrode of the electrode array, based in part on a decision whether to continue the sampling run, indicated at 131*g*. The electrical property may be measured for each sampling electrode only once before application of a lysis voltage to the sampling electrode, or the electrical property may be monitored over time, such as at regular intervals, before the lysis voltage is applied to the sampling electrode. In some cases, the electrical property may continue to be monitored only for the sampling electrodes of the electrode array that have not yet received the lysis voltage. Accordingly, all of the sampling electrodes may be monitored at first, and then fewer and fewer may be monitored over time as an increasing number of the sampling electrodes have received the lysis voltage followed by electrophoresis voltage. In some examples, the sampling run may stop automatically, when at least a threshold number of sampling electrodes have received the lysis voltage. In some examples, the user may stop the sampling run based on predicted-capture data that has been outputted to the user. For example, the user may decide to abort the sampling run early if the predicted-capture data indicates the presence of a technical problem.

Nucleic acids may be tagged with structurally different tags at a plurality of the sampling electrodes (and/or in corresponding wells), indicated at 131$h$. One or more reagents for performing a tagging reaction, such as reagents for a reverse transcription reaction, may be received on the chip adjacent the electrode array. The nucleic acids tagged may be nucleic acids captured at step 131$d$, complements of these captured nucleic acids, or fragments of these captured nucleic acids. Each structurally different tag at one of the sampling electrodes of the plurality of sampling electrodes may include a different nucleotide sequence including an identifier. In some examples, the tag may be a primer and tagging may be achieved by extending the primer to synthesize complements of captured RNA molecules at the sampling electrode, where the complements are covalently linked to the identifier. This primer extension may be catalyzed by a reverse transcriptase enzyme. In other examples, tagging may be achieved by covalently attaching the identifier to captured nucleic acids or fragments thereof.

A library of tagged nucleic acids may be prepared, indicated at 131$i$. The library may represent tagged nucleic acids from a plurality of the sampling electrodes (and/or corresponding wells). Library construction may include releasing and pooling tagged nucleic acids from the plurality of sampling electrodes and/or corresponding wells, adding linkers to tagged nucleic acids, transcribing tagged nucleic acids in vitro with an RNA polymerase, amplifying tagged nucleic acids using PCR, or any combination thereof, among others. Members of the library may be sequenced to obtain a nucleotide sequence from each member. The nucleotide sequence may include a sequence of the identifier of one of the tags (or a perfect complement thereof) and a sequence from a nucleic acid released by a cell aligned with the tag, or from a complement of the nucleic acid.

III. EXAMPLES

The following examples describe selected exemplary aspects and features of the methods, systems, and devices of the present disclosure related to sampling/isolating nucleic acids from cells using an array of sampling electrodes. These examples are intended for illustration only and should not limit the scope of the disclosure. The aspects and features described in this section may be combined with one another and with any combination of the aspects and features of the methods, systems, and devices disclosed elsewhere herein, such as in Sections I, II, and IV.

Example 1

Illustrative Electrical Measurements

Figure 4:
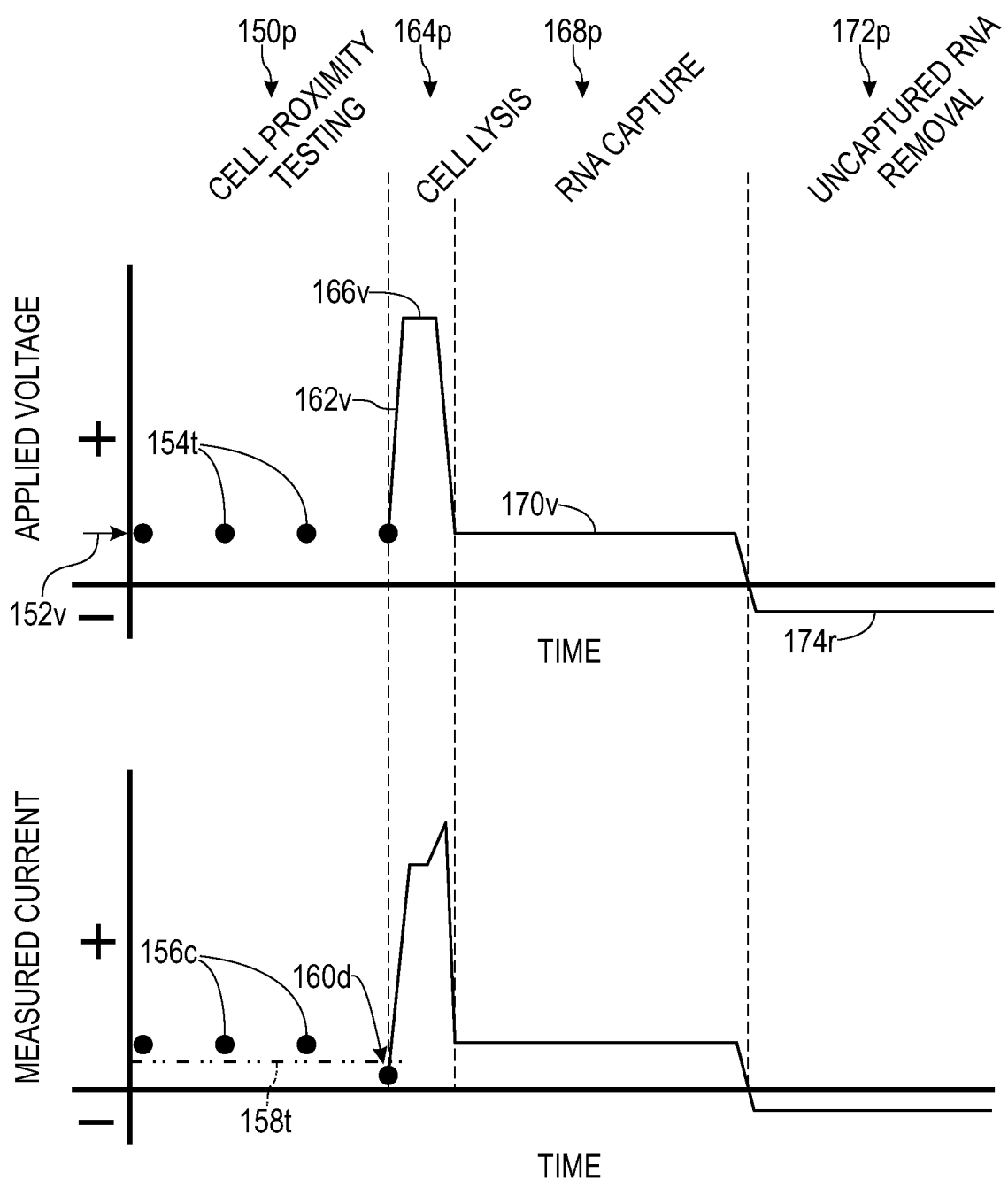
FIG. 4 is a pair of graphs showing illustrative voltage that may be applied to a sampling electrode of an array of sampling electrodes over a time period during performance of the method of FIG. 3, and illustrative electric current that may be measured from the sampling electrode for the same time period.
Figure 5:
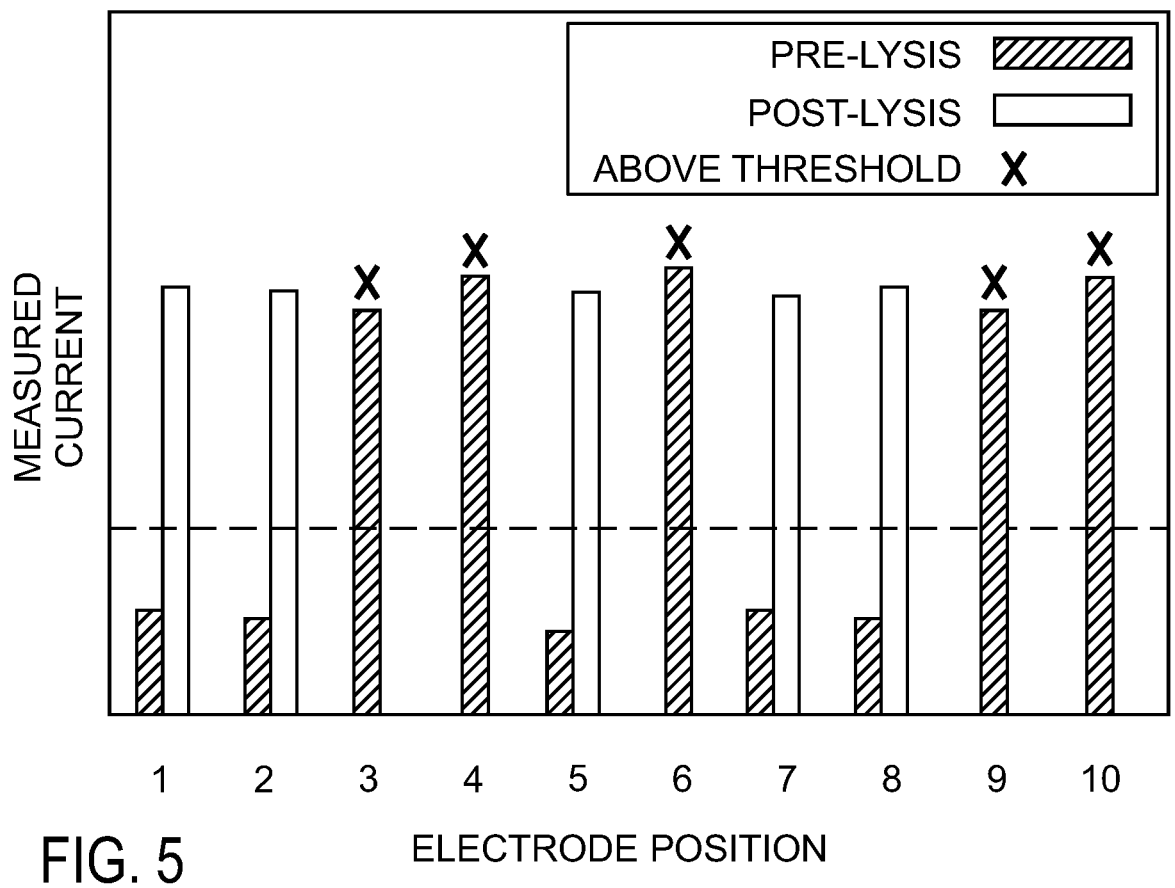
FIG. 5 is a graph plotting illustrative electric current that may be measured from ten sampling electrodes of an array of sampling electrodes during performance of the method of FIG. 3.
Figure 6:
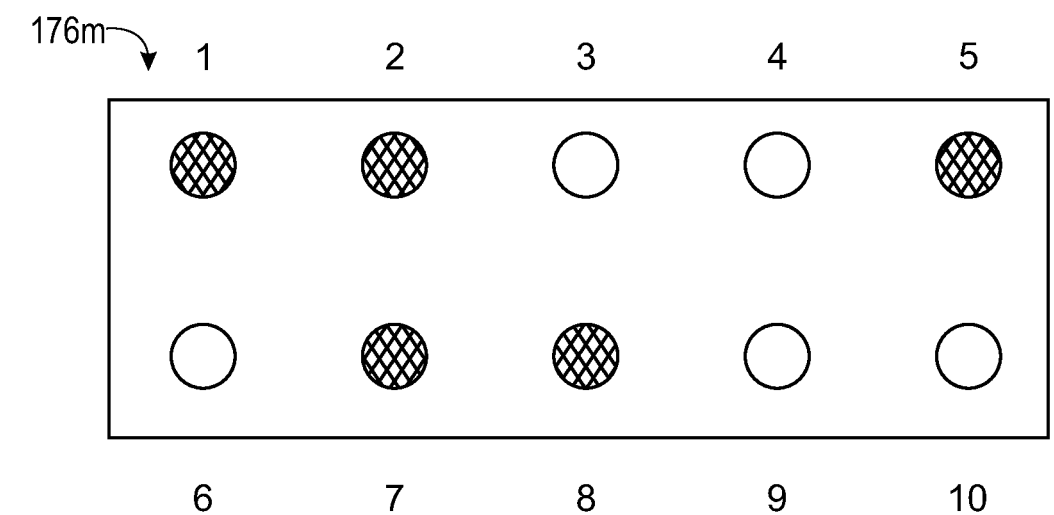
FIG. 6 is an exemplary capture prediction map that may be generated during performance of the method of FIG. 3 using the data plotted in the graph of FIG. 5.

This example describes illustrative electrical measurements that may be recorded with an exemplary embodiment of sampling system 50 by performance of an exemplary implementation of sampling method 130 in which RNA released by cell lysis is captured by hybridization to a complementary capturing agent; see FIGS. 4-6 (also see FIGS. 1-3).

FIG. 4 shows a pair of temporally aligned graphs presenting voltage and electric current over the same time period for a single sampling electrode of an electrode array of the sampling system. The sampling electrode is located at the bottom of a well. The upper graph plots the voltage applied to the sampling electrode over the time period, and the lower graph plots electric current that may be measured from the electrode for the same time period.

Cell proximity testing may be performed during a testing phase 150$p$ of the time period. A positive test voltage 152$v$ may be applied to the sampling electrode (i.e., the sampling electrode is positive (the anode) and a counter electrode is negative (the cathode)). The test voltage may be applied continuously or as one or a series of test pulses 154$t$, which may be applied at regular intervals. Test pulses 154$t$ may produce a temporally matching series of one or more measured current pulses 156$c$ at the sampling electrode. Each measured current pulse 156$c$ may be compared with a threshold 158$t$. Test pulses 154$t$ may be continued until a measured current pulse 156$c$ drops below threshold 158$t$, indicated by an arrow at 160$d$. This decrease in measured current indicates an increase in electrical resistance between the sampling electrode and the counter electrode, resulting from a cell being in very close proximity to the well over the sampling electrode. (The cell may at least partially seal the mouth of the well with its plasma membrane (or wall).) The decrease in measured current also indicates that the membrane/wall of the cell should be easier to rupture upon application of a predefined lysis voltage, due to a reduced electrolyte/conductor cross section between the cell and the lip of the well. Furthermore, the decrease in measured current indicates that nucleic acids from the cell can be captured in the well once the cell is lysed.

A voltage spike 162$v$ may be applied to start a cell lysis phase 164$p$, once the measured electric current drops below threshold 158$t$. Voltage spike 162$v$ may reach a lysis voltage 166$v$ that is significantly higher than the voltage of test pulses 154$t$, such as at least 50%, 75%, 100%, 150%, 200%, 500%, 1000%, or 2000% higher, among others. Moreover, the measured current may increase disproportionately, as shown, relative to the applied voltage, if cell lysis occurs, because the lysed cell offers less resistance to the flow of electric current. The drop in measured electric current below threshold 158$t$ may occur stochastically over time and may be stochastically reversible, too. Accordingly, application of voltage spike 162$v$ may commence immediately once the measured current drops below threshold 158$t$. The possible stochastic nature of this current drop means that different sampling electrodes of the electrode array may exhibit a current drop below threshold 158$t$ at different times relative to one another. Accordingly, the various phases shown here may not be performed in parallel among sampling electrodes of the electrode array.

An RNA capture phase 168$p$ may be initiated at the end of lysis phase 164$p$. An electrophoresis voltage 170$v$ may be applied to the sampling electrode, with the same voltage polarity as testing phase 150$p$ and lysis phase 164$p$. Electrophoresis voltage 170$v$ drives nucleic acids including RNA toward the sampling electrode because the nucleic acids are negatively charged. The RNA can be captured by the capturing agent over the sampling electrode and/or in the well. The level of electrophoresis voltage 170$v$ may be significantly less than lysis voltage 166$v$, such as less than 50% of lysis voltage 166v. Here, electrophoresis voltage 170v is at the same level as test voltage 152v, but in other examples, electrophoresis voltage 170v may be higher or lower than test voltage 152v. Electrophoresis voltage 170v may be applied continuously or as a series of electrophoretic pulses, among others. Since electrophoresis voltage 170v is applied at the same level as test voltage 152v in this example, the measured current after cell lysis can be compared directly with the measured current before cell lysis. Consistent with cell lysis having occurred, the measured current during RNA capture phase 168p may remain fairly constant, with no further fluctuations below threshold 158t.

A purification phase 172p may be initiated after RNA capture phase 168p. A reverse voltage 174r may be applied to the sampling electrode, to drive uncaptured nucleic acids away from the sampling electrode and out of the well. Reverse voltage 174r has a polarity opposite that of electrophoresis voltage 170v and may have any suitable magnitude relative to electrophoresis voltage 170v. The absolute value of reverse voltage 174r may be less than that of electrophoresis voltage 170v, as shown here, or may be the same as or greater than that of electrophoresis voltage 170v. The level of reverse voltage 174r may be selected to balance the competing concerns of more efficient removal of unbound nucleic acids using a higher reverse voltage against more efficient retention of captured RNA during this phase using a lower reverse voltage.

FIG. 5 shows a graph plotting illustrative electric current that may be measured from only a small subset (ten) of sampling electrodes of the electrode array during performance of the exemplary sampling method. The pre-lysis electric current for each electrode is represented by hatched bars. Hatched bars without an adjacent "X" report the measured electric current below threshold 158t that triggered application of a lysis voltage for the indicated sampling electrode. Hatched bars topped by an "X" report the lowest measured electric current for the indicated sampling electrodes. Unfilled bars report the post-lysis electric current measured after application of the lysis voltage, using the same test voltage as for the pre-lysis current measurements. Sampling electrodes for which the lysis voltage has not been applied do not have an unfilled bar accompanying the hatched bar because there is no post-lysis current to report. Electrodes at positions 1, 2, 5, 7, and 8 have received the lysis voltage and, after application of the lysis voltage, exhibit a post-lysis current comparable to the pre-lysis current of electrodes 3, 4, 6, 9, and 10.

FIG. 6 shows an exemplary predicted-capture map 176m that may be generated from the data of FIG. 5 in real time during performance of the exemplary sampling method. Predicted-capture map 176m shows where RNA is predicted to have been captured according to electrode position, based on which sampling electrodes have received the lysis voltage. More specifically, sampling electrodes 1, 2, 5, 7, and 8 are represented by cross-hatched circles, and sampling electrodes 3, 4, 6, 9, and 10 are represented by unfilled circles. Since the sampling system may have an electrode array of thousands of electrodes, the predicted-capture map may, for example, use color coding to indicate different percentages of sampling electrodes that are predicted to have captured RNA, for different sections of the electrode array.

Example 2

Electrode, Well, and Circuit Configurations

This example describes exemplary configurations for electrodes, wells, and associated energization/sensing circuits for the methods, systems, and devices of the present disclosure; see FIGS. 7, 8, 9A, 9B, and 10-14.

Figure 7:
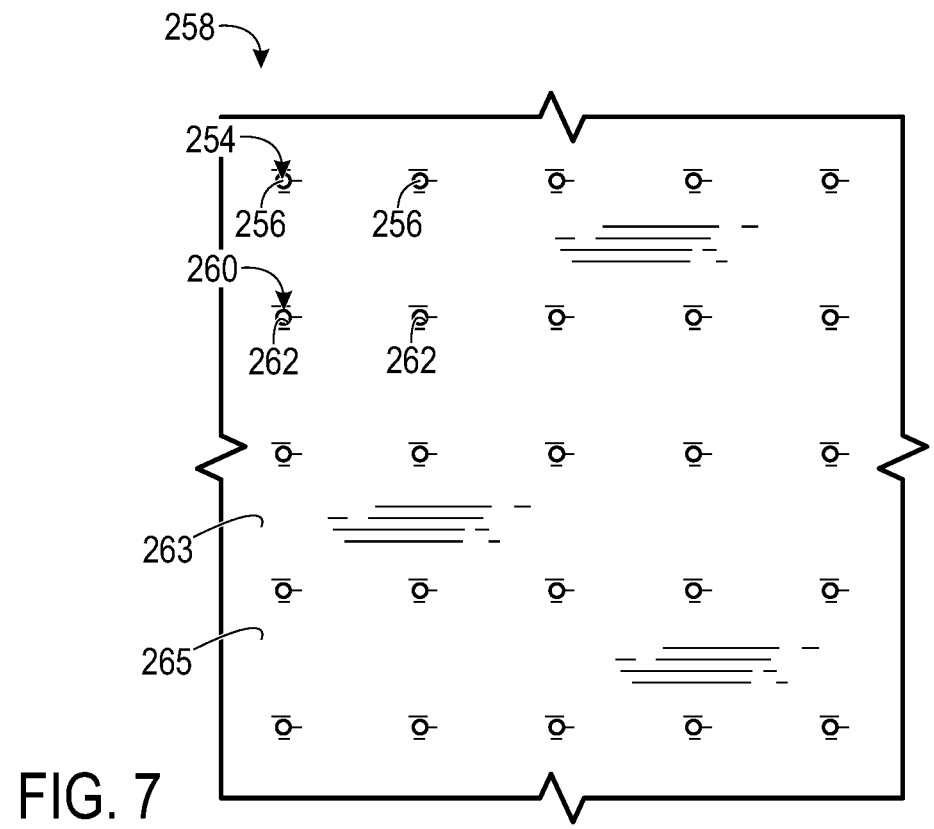
FIG. 7 is a fragmentary, top plan view of an exemplary chip for the methods, systems, and devices of the present disclosure, where the chip has an array of sampling electrodes each located at the bottom of a different well.

FIG. 7 shows a fragmentary portion of an exemplary embodiment (chip 258) of chip 58 (also see FIG. 1). Chip 258 has a rectangular electrode array 254 of sampling electrodes 256, which may be regularly spaced along each of two orthogonal axes, with the same spacing along both axes. The chip defines a corresponding, vertically aligned well array 260 of wells 262, which are formed in a top surface 263 of chip 258. Each sampling electrode 256 of electrode array 254 is located at the bottom of a different well 262 of well array 260. Wells 262 may be defined at least partially in a dielectric layer 265 of chip 258, such that the wells are electrically insulated from one another laterally. The center-to-center spacing between wells 262 may be greater than the diameter of wells 262. For example, in the depicted embodiment, the well spacing is ten times the well diameter.

Figure 8:
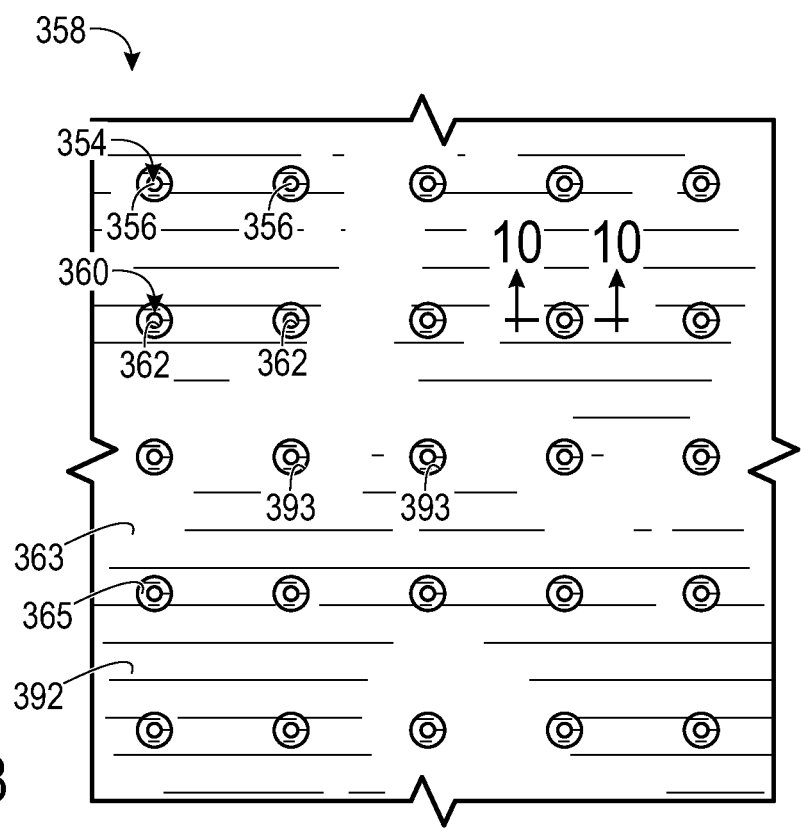
FIG. 8 is a fragmentary, top plan view of another exemplary chip for the methods, systems, and devices of the present disclosure, where the chip is similar to that of FIG. 7, except for the addition of a single guard electrode encircling each of the different wells.

FIG. 8 shows a fragmentary portion of another exemplary embodiment (chip 358) of chip 58 (also see FIG. 1). Chip 358 has a rectangular electrode array 354 of sampling electrodes 356 similar to that of FIG. 7, and a well array 360 of wells 362. Wells 362 are formed in a dielectric layer 365, and in a top surface 363 of chip 358. Chip 358 also has a single guard electrode 392 located on dielectric layer 365. Guard electrode 392 may be formed of a plated conductive material. Guard electrode 392 defines a plurality of openings 393 each aligned with (centered on) one of sampling electrodes 356 and a corresponding well 362. Openings 393 are larger in diameter than sampling electrodes 356 and wells 362. This difference in diameter helps to electrically isolate each sampling electrode 356 from guard electrode 392, to avoid interference between these two types of electrodes. When wells 362 and guard electrode 392 are projected vertically onto the same horizontal plane to form a projection, guard electrode 392 encircles each sampling electrode 356 and well 362 in the projection. Guard electrode 392 reduces or prevents conduction (i.e., electrical leakage) between wells 362. Accordingly, the guard electrode allows each well 362 to have an electrical signal that is substantially unaffected by adjacent wells 362, which allows a higher density of wells 362 (i.e., a smaller ratio of well spacing to well diameter). A guard voltage is applied to guard electrode 392 and may be set to optimize the sampling of nucleic acids from a tissue section, while reducing or preventing conduction between wells 362. For example, guard electrode 392 may be set to the same electric potential as wells 362, or may be set to a different electric potential, such as the electric potential at the bottom of a section of tissue above wells 362.

Figure 9A:
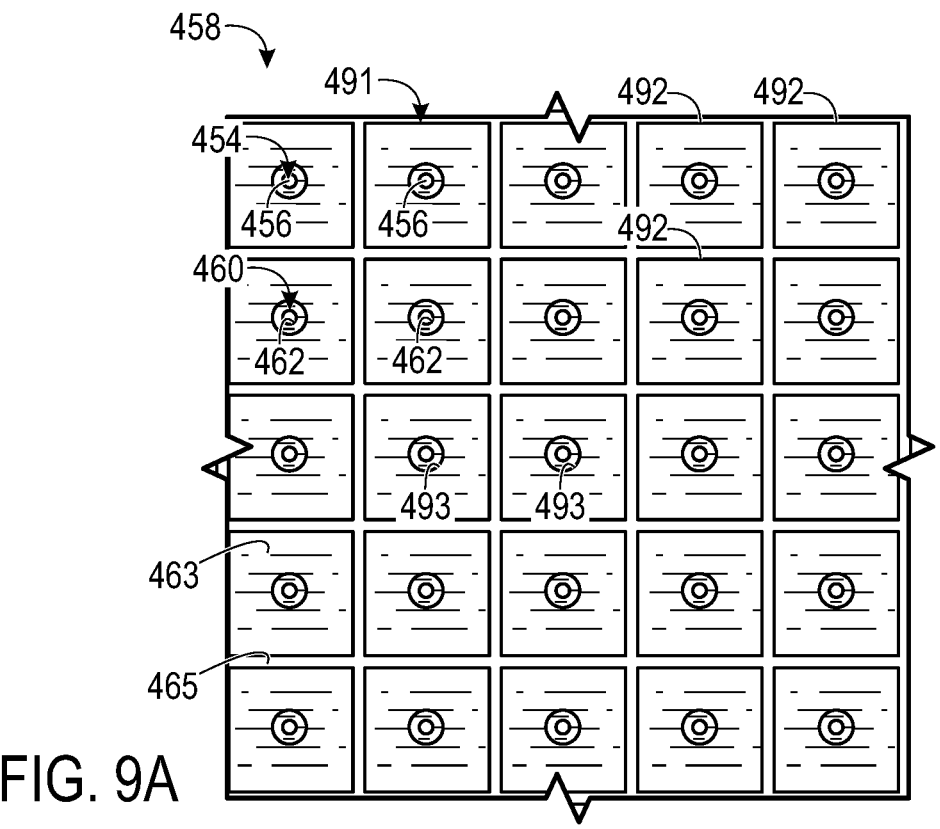
FIG. 9A is a fragmentary, top plan view of yet another exemplary chip for the methods, systems, and devices of the present disclosure, where the chip is similar to that of FIG. 8, except that the chip has a plurality of guard electrodes collectively encircling each of the different wells and each individually encircling only one of the different wells.

FIG. 9A shows a fragmentary portion of yet another exemplary embodiment (chip 458) of chip 58 (also see FIG. 1). Chip 458 has a rectangular electrode array 454 of sampling electrodes 456 similar to that of FIG. 8, and a well array 460 of wells 462 formed in a top surface 463 of the chip, in a dielectric layer 465 thereof. However, instead of having a single guard electrode, as in chip 358 of FIG. 8, chip 458 has a guard electrode array 491 including a separate guard electrode 492 located around each well 462 and defining an opening 493 aligned with the well. Like guard electrode 392 of FIG. 8, guard electrode array 491 reduces or prevents conduction (i.e., electrical leakage) between wells 462. Accordingly, guard electrode array 491 allows each well 462 to have an electrical signal that is unaffected by surrounding wells 462, which allows a higher density of wells 462. An advantage of guard electrode array 491, relative to single guard electrode 392 discussed above is that guard electrodes 492 are independently controllable by the control circuit. Accordingly, a different guard voltage can be applied to the respective guard electrode 492 around each well 462. For example, the respective guard electrode may be set to the electric potential at the well 462 or to another value such as the electric potential at the bottom of a tissue section located on chip 458. Guard electrode array 491 allows the electric potential of each guard electrode 492 to be optimized for spatial variation in the tissue section.

Figure 9B:
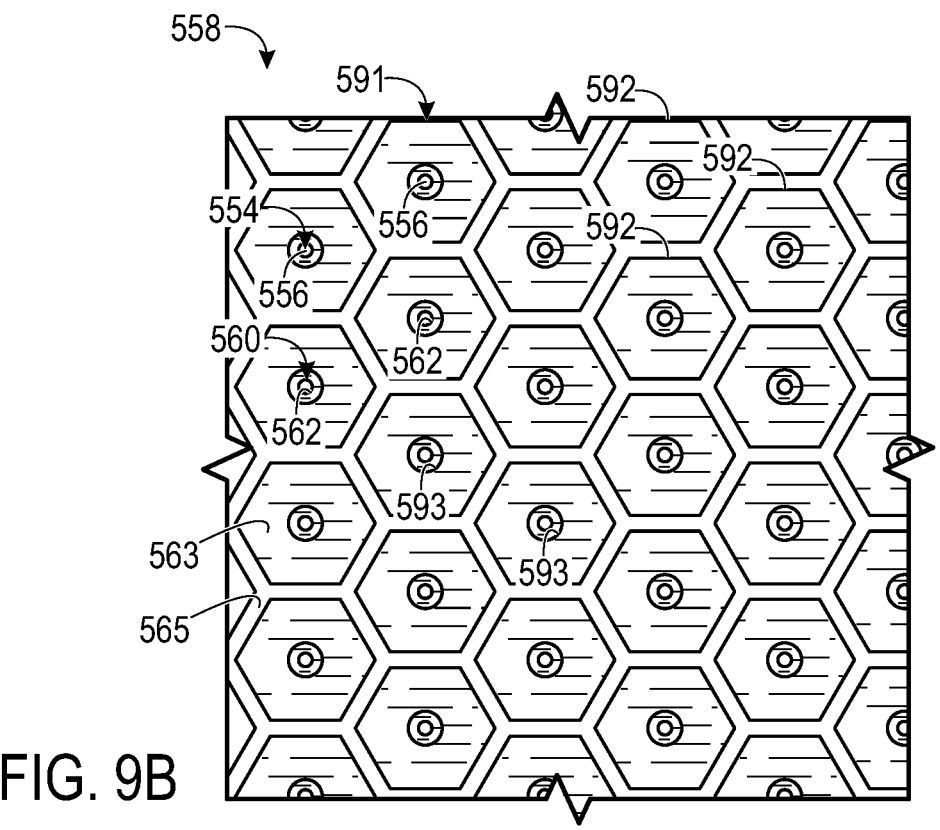
FIG. 9B is a fragmentary, top plan view of still another exemplary chip for the methods, systems, and devices of the present disclosure, where the chip is similar to that of FIG. 9A, except that the sampling electrodes, wells, and guard electrodes are arranged in a hexagonal array instead of a rectangular array.

FIG. 9B shows a fragmentary portion of still another exemplary embodiment (chip 558) of chip 58 (also see FIG. 1). Chip 558 has a hexagonal electrode array 554 of sampling electrodes 556, and a corresponding hexagonal well array 560 of wells 562 formed in a top surface 563 of the chip, in a dielectric layer 565 thereof. This hexagonal arrangement allows electrode array 554 and well array 560 to be more compact. Chip 558 has a guard electrode array 591 of individually controllable guard electrodes 592 similar to guard electrodes 492 described above for FIG. 9A, with each guard electrode 592 located around a different well 562 and defining an opening 593 centered on the well.

Figure 10:
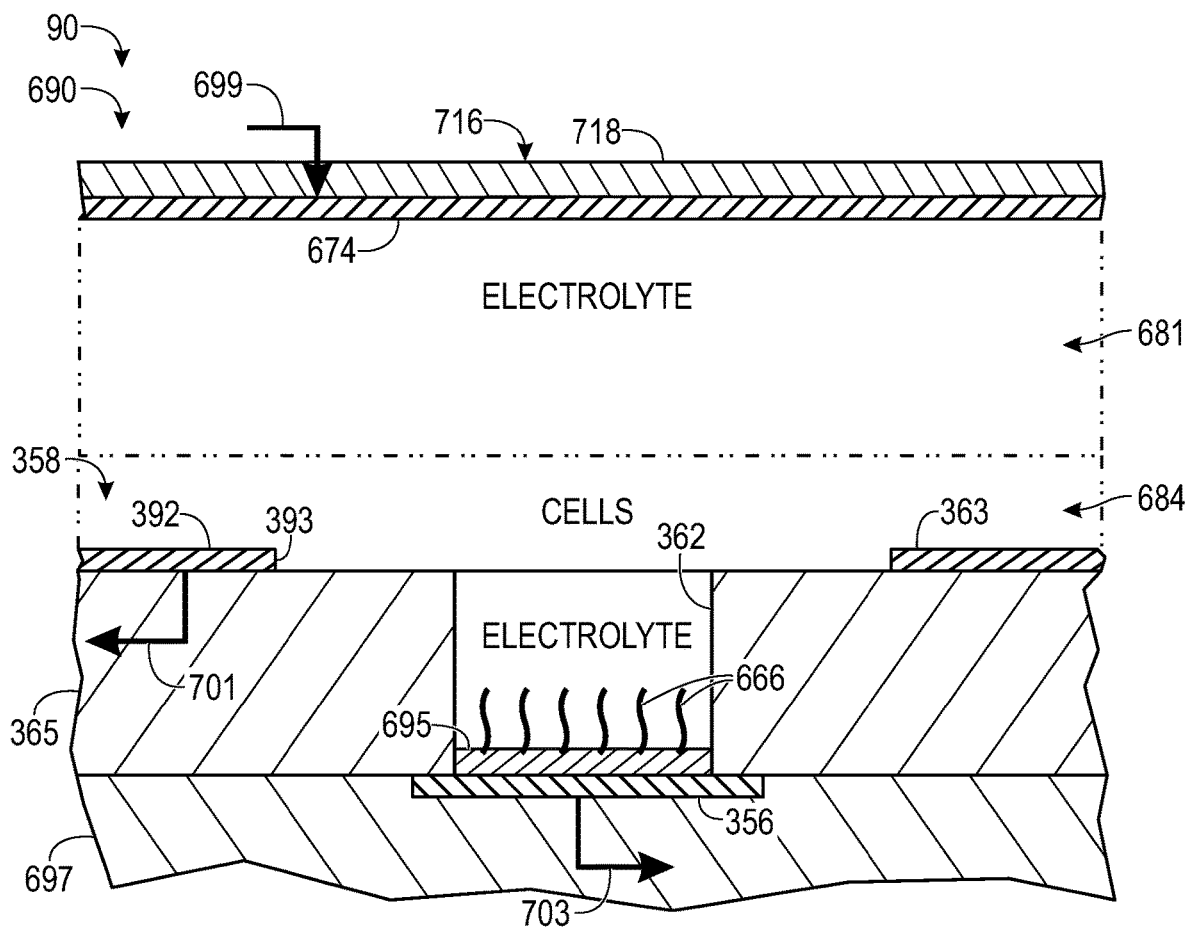
FIG. 10 is a fragmentary, sectional view of an exemplary isolation device including the chip of FIG. 8 and a removable cover providing a shared counter electrode, taken generally along line 10-10 of FIG. 8 through one of the wells and a corresponding sampling electrode.

FIG. 10 shows a portion of an exemplary embodiment (isolation device 690) of isolation device 90 including chip 358 of FIG. 8 (also see FIG. 2). The portion of chip 358 shown includes one sampling electrode 356, one aligned well 362, and top surface 363 and dielectric layer 365 in which well 362 is formed.

Guard electrode 392 is also shown, including an opening 393 therein aligned with well 362. Opening 393 may have an opening diameter that is substantially larger than the diameter of the mouth (top) of well 362, such as an opening diameter that is at least 1.5, 2, or 3 times the well diameter.

Copies of one tag 666 of a tag array of different tags (i.e., having different identifiers relative to one another) are located in well 362. The copies are attached to sampling electrode 356 via a porous layer 695 located on the sampling electrode. Porous layer 695 immobilizes the copies of tag 666 so that they remain connected to sampling electrode 356 and in well 362 during the sampling run, even if a reverse voltage is applied to the sampling electrode. The porous layer permits contact of the electrolyte with sampling electrode 356, optionally while preventing nucleic acids from reaching the sampling electrode. Porous layer 695 may be located in well 362, such as in a lower portion thereof, as shown here, and may, for example, be a hydrogel.

A substrate 697 is located under dielectric layer 365, optionally in contact with the dielectric layer. Substrate 697 may be formed of a semiconductor. Sampling electrode 356 may be located over, on, and/or in substrate 697 and at the bottom of well 362. The sampling electrode may (or may not) form at least part of the floor of well 362, as shown here.

Isolation device 690 has a cover 716 including a body 718 and a counter electrode 674, which is attached to an underside of the body. An electrolyte-receiving space 681 and a cell-receiving area 684 are located between counter electrode 674 and top surface 363 of chip 358. A tissue section may be received on top surface 363, namely, on guard electrode 392 and dielectric layer 365, where the dielectric layer is not covered by the guard electrode and defines the side wall portion of well 362. An electrolyte provides electrical contact between counter electrode 674 and the tissue section, and between the tissue section and sampling electrode 356.

Electrical connections of the different types of electrodes 356, 392, and 674 to circuit portions of a control circuit are also shown. Counter electrode 674 connects to voltage reference electronics at 699. Guard electrode 392 connects to guard electronics at 701. Sampling electrode 356 connects to sampling electronics at 703.

FIGS. 11-14 show circuit portions of exemplary control circuits. Each circuit portion enables setting one or more voltages and/or sensing current.

Figure 11:
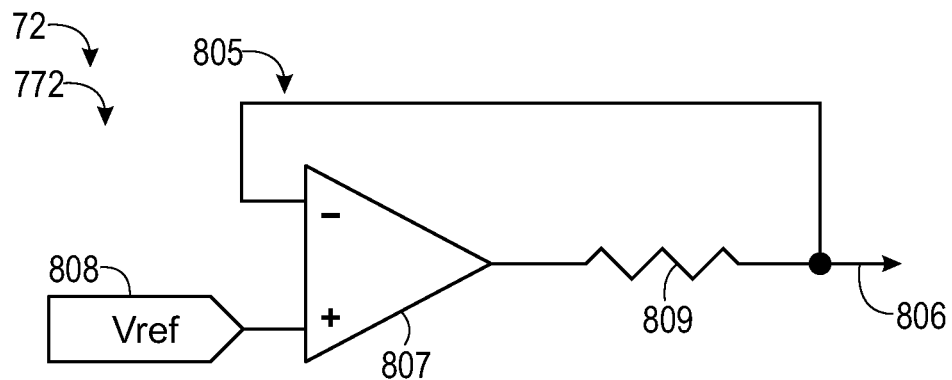
FIG. 11 is a circuit diagram of an exemplary circuit portion for the control circuit of the sampling system of FIG. 1, wherein the circuit portion may be utilized to set the voltage bias of the counter electrode of FIGS. 1 and 10 or to set the voltage bias of the guard electrode of FIG. 10.

FIG. 11 shows a circuit diagram of an exemplary circuit portion 805 of an embodiment (control circuit 772) of control circuit 72 of sampling system 50 of FIG. 1. Circuit portion 805 may be utilized to set the voltage bias of a counter electrode, such as counter electrode 74 or 674 (see FIGS. 1, 2, and 10), or of a guard electrode, such as guard electrode 392 (see FIGS. 8 and 10).

Circuit portion 805 has an output 806 operably coupled to a counter electrode or guard electrode (e.g., at 699 or 701 in FIG. 10). An operational amplifier 807 has a voltage reference set on the positive input ('+') by a voltage reference (Vref) 808, such as a digital-to-analog converter (DAC). The voltage set by voltage reference 808 is driven to output 806 through an optional resistor 809. Output 806 also provides negative feedback to the negative input ('−') of operational amplifier 807, such that output 806 matches the voltage set by voltage reference 808. Resistor 809, if included, serves as a current sense resistor for the counter electrode or guard electrode, with sense electronics not illustrated here. If included, resistor 809 is set to a small value (e.g., $0.1\Omega$ to $100\Omega$) with a value based on the maximum current sampled. If current sensing is not needed, then resistor 809 may be omitted from circuit portion 805 or set to zero ohms ($0\Omega$).

Figure 12:
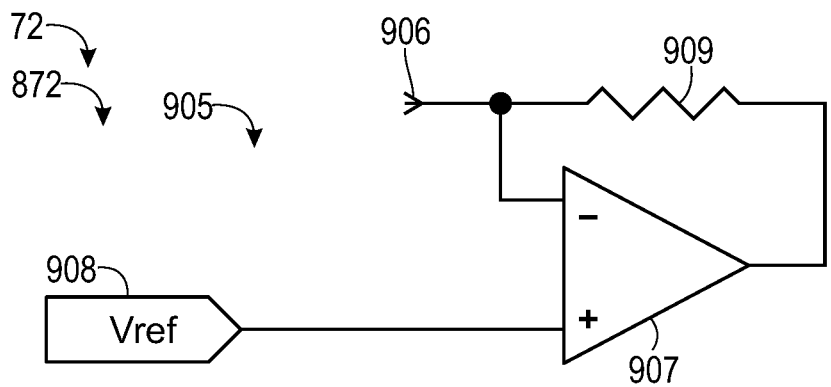
FIG. 12 is a circuit diagram of an exemplary circuit portion for the control circuit of the sampling system of FIG. 1, where the circuit portion may be utilized to set the voltage bias of the guard electrodes of FIGS. 9A and 9B.

FIG. 12 is a circuit diagram of an exemplary circuit portion 905 for an embodiment (control circuit 872) of control circuit 72 of sampling system 50 of FIG. 1. Circuit portion 905 may be utilized to set the voltage bias of segmented guard electrodes 492, 592 of FIGS. 9A and 9B.

Circuit portion 905 has an output 906 operably coupled to guard electrodes 492 or 592. An operational amplifier 907 has a voltage reference set on the positive input ('+') by a voltage reference (Vref) 908, such as a digital-to-analog converter (DAC). The voltage set by voltage reference 908 is driven to output 906 through optional resistor 909. Output 906 also provides negative feedback to negative input ('−') of operational amplifier 907, such that output 906 matches the voltage set by voltage reference 908. Resistor 909, if included, serves as a current sense resistor for segmented guard electrodes 492 or 592, with sense electronics not illustrated here. If included, resistor 909 is set to a small value (e.g., $0.1\Omega$ to $100\Omega$) with a value based on the maximum current sampled. If current sensing is not needed, then resistor 909 may be omitted from the circuit or set to zero ohms ($0\Omega$).

Figure 13:
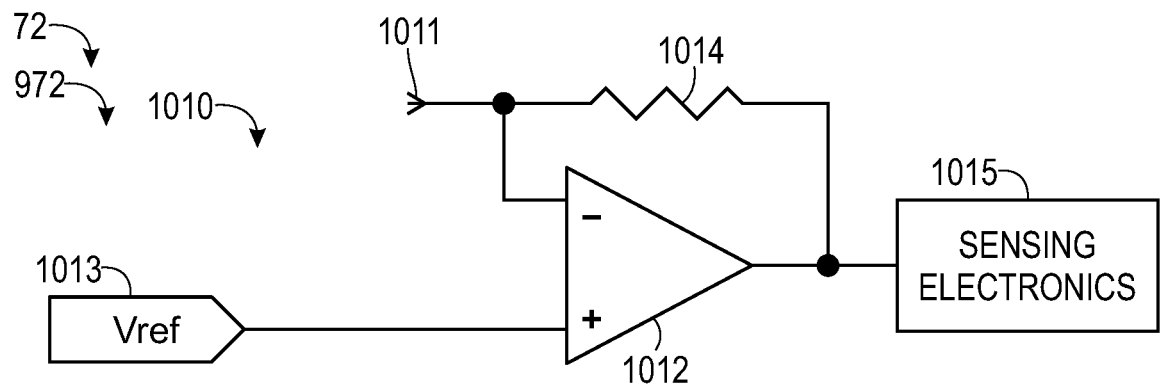
FIG. 13 is a circuit diagram of an exemplary circuit portion for the control circuit of the sampling system of FIG. 1, where the circuit portion may be utilized to set the voltage bias and sense the current of sampling electrodes of the sampling system.

FIG. 13 is a circuit diagram of an exemplary transimpedance amplifier circuit 1010 for an embodiment (control circuit 972) of control circuit 72 of sampling system 50 of FIG. 1. Amplifier circuit 1010 may be utilized to set the voltage bias and sense the current of sampling electrodes 56, 256, 356, 456, or 556 of the sampling system (also see FIGS. 1, 5-8, 9A, and 9B). An output 1011 is operably coupled to a sampling electrode. Amplifier circuit 1010 both drives the voltage of the sampling electrode and senses the current thereof. An operational amplifier 1012 has a voltage reference set on the positive input ('+') by a voltage reference (Vref) 1013, such as a digital-to-analog converter (DAC). The voltage set by voltage reference 1013 is driven to output 1011 through the negative feedback to the negative input ('−') of operational amplifier 1012, such that output 1011 matches the voltage set by voltage reference 1013. A resistor 1014 serves as a current sense resistor for current sensing electronics 1015 to sense the current of the sampling electrode. Based on Ohm's law, the current of the sampling electrode is determined by the difference between the output of operational amplifier 1012 and voltage reference 1013, divided by the resistance value of resistor 1014. Operational amplifier 1012 may have a very low input bias current, such that the current going into the negative input ('−') of the operational amplifier is insignificant compared to the sensed current of the sampling electrode.

Figure 14:
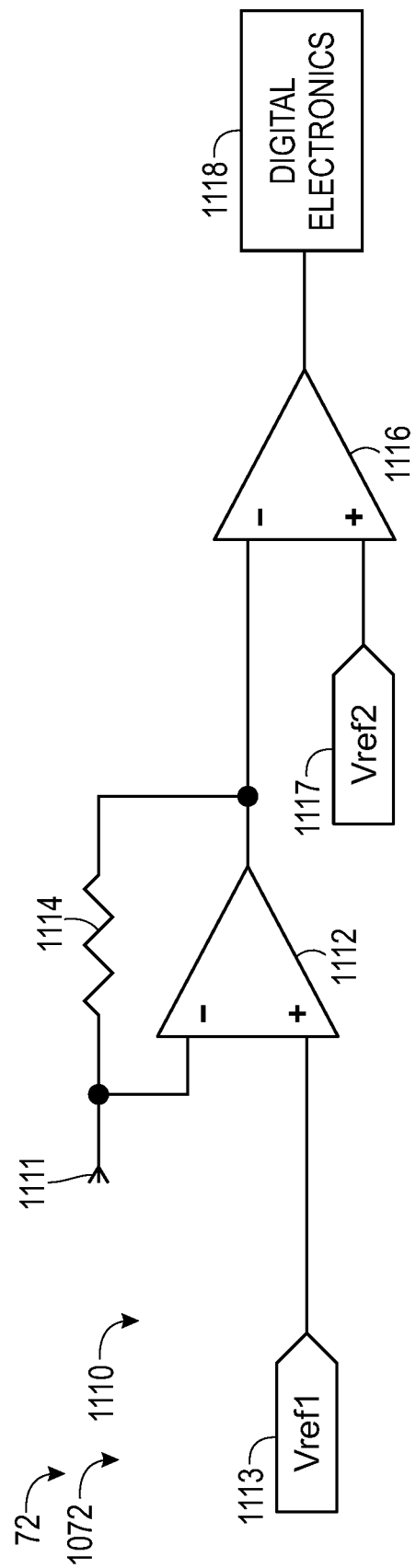
FIG. 14 is a circuit diagram of another exemplary circuit portion for the control circuit of the sampling system of FIG. 1, where the circuit portion may be utilized to set the voltage bias and sense the current of sampling electrodes of the sampling system.

FIG. 14 is a circuit diagram of an exemplary transimpedance amplifier circuit 1110 for an embodiment (control circuit 1072) of control circuit 72 of sampling system 50 of FIG. 1. Amplifier circuit 1110 may be utilized to set the voltage bias and sense the current of sampling electrodes 56, 256, 356, 456, or 556 of the sampling system (also see FIGS. 1, 5-8, 9A, and 9B). An output 1111 is operably coupled to the sampling electrode. Amplifier circuit 1110 drives the voltage of the sampling electrode and senses current of the sampling electrode. An operational amplifier 1112 has a voltage reference set on the positive input ('−') thereof by a first voltage reference (Vref1) 1113, such as a digital-to-analog converter (DAC). The voltage set by first voltage reference 1113 is driven to output 1111 through negative feedback to the negative input ('−') of operational amplifier 1112, such that output 1111 matches the reference voltage set by first voltage reference 1113. A resistor 1114 serves as a current sense resistor for the sampling electrode, where the current sensing electronics are comprised of a comparator 1116, a second voltage reference (Vref2) 1117, and digital electronics 1118. Based on Ohm's law, the current of the sampling electrode is determined by the difference between the output of operational amplifier 1112 and the value of first voltage reference 1113 divided by the resistance value of resistor 1114. Operational amplifier 1112 may have a very low input bias current, such that the current going into the negative input ('−') of the operational amplifier is insignificant compared to the sensed current of the sampling electrode. Second voltage reference 1117 is set to a value that causes comparator 1116 to change state when the target current for the sampling electrode is achieved.

The electronics of the sampling system may have any suitable configuration and distribution among system components. In some examples, the sampling system may have an independent voltage reference for each sampling electrode and independent sensing electronics including a comparator, an ND, or both, such as the circuit depicted in FIG. 13. This may be a complex system with an expensive implementation. The more expensive electronic components (voltage reference and A/D) may be on independent equipment or a reusable chip carrier. The chip may be disposable (single-use) or reusable. The chip carrier may use a rechargeable battery or external source of power. In other embodiments, all of the electronics may be integrated onto the chip, which may be disposable (single-use) or reusable. In some examples, the sampling system may include shared voltage references and multiplexers (Mux) for sampling electrodes, shared sensing electronics that are multiplexed (Mux) including a comparator, ND, or both, such as the circuit in FIG. 13. In still other embodiments, the sampling system may have shared voltage references and multiplexers (Mux) for the sampling electrodes and a comparator for each sampling electrode, with no expensive sensing electronics such as an ND, as depicted in FIG. 14.

Example 3

Isolation Device for Sampling Nucleic Acids From Cells

Figure 15:
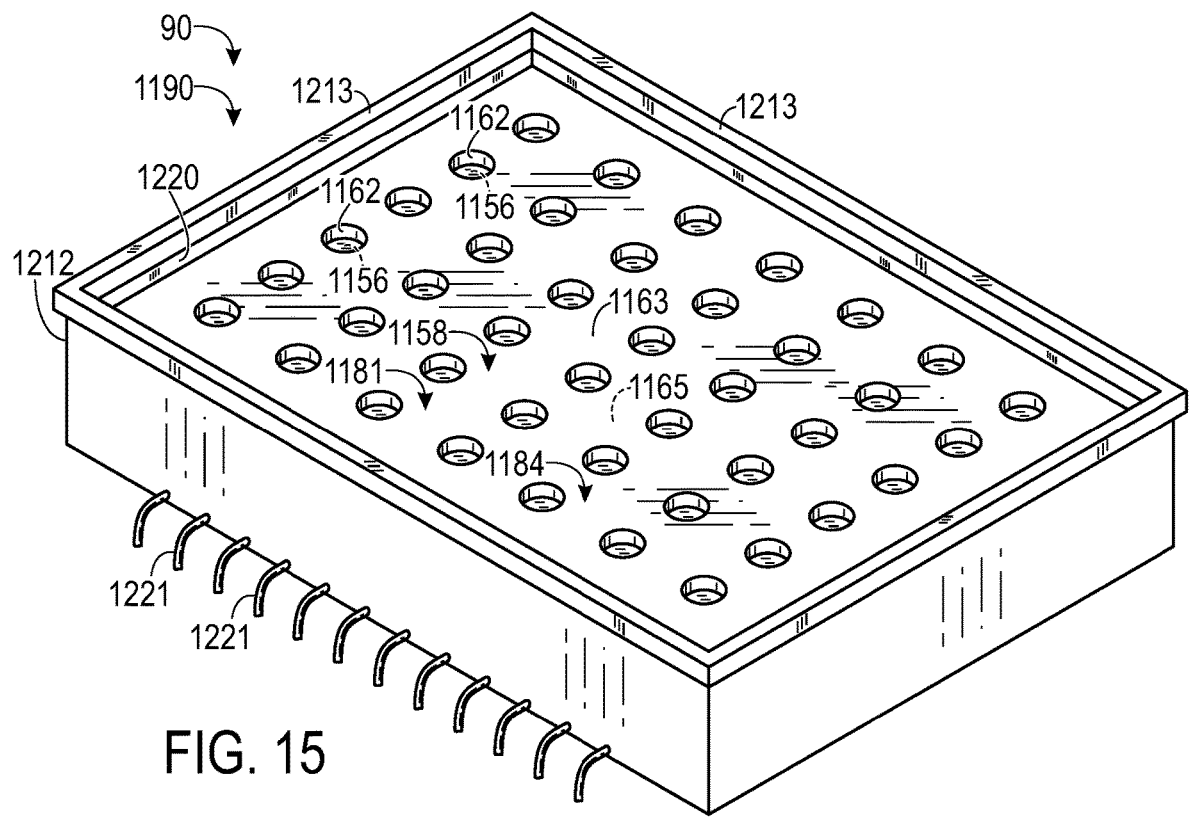
FIG. 15 is an isometric view of an exemplary isolation device for the sampling system of FIG. 1, with a cover of the isolation device removed, and with the isolation device having only a small number of wells and corresponding sampling electrodes for clarity.
Figure 16:
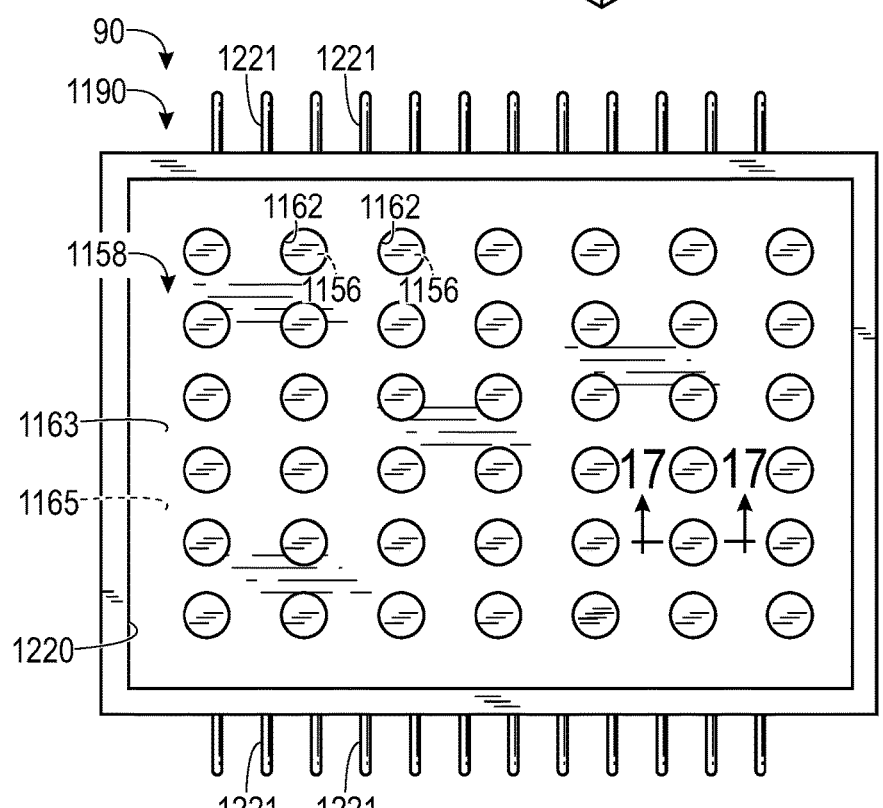
FIG. 16 is a top plan view of the isolation device of FIG. 15.
Figure 17:
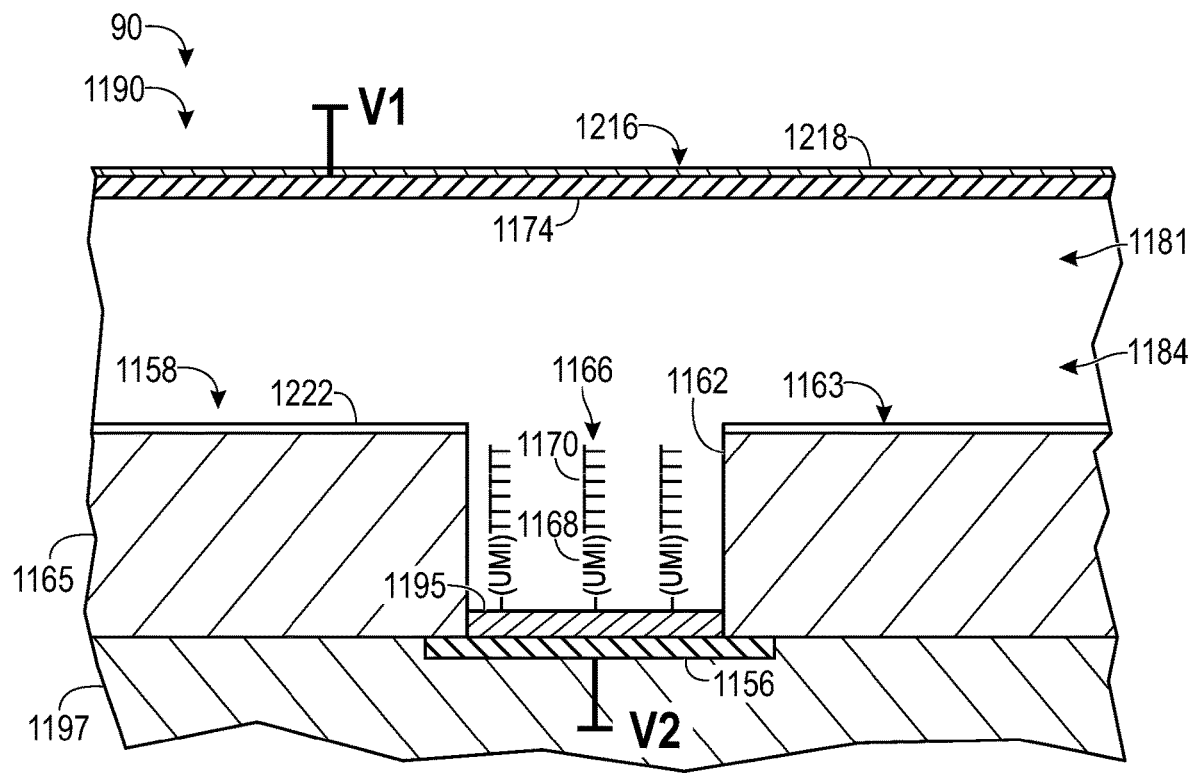
FIG. 17 is a fragmentary sectional view of the isolation device of FIG. 15, taken generally along line 17-17 of FIG. 16 is the presence of the cover.

This example describes an exemplary embodiment, isolation device 1190, of isolation device 90 for the systems and methods of the present disclosure; see FIGS. 15-17 (also see FIG. 2).

Isolation device 1190 has a chip 1158 forming an array of sampling electrodes 1156 aligned with an array of wells 1162 (see FIGS. 15 and 16). The size of each array (i.e., forty-two members) is small for clarity, namely, to make individual wells 1162 easily visible in the context of the entire isolation device 1190. Chip 1158 has a top surface 1163 in which wells 1162 are formed, with each well having a side wall portion formed in a dielectric layer 1165, which may or may not form the lip of the well.

A housing 1212 of isolation device 1190 has side walls 1213 extending above chip 1158. Side walls 1213 serve as a barrier to lateral flow of fluid and create a side wall portion of a vessel 1220. Top surface 1163 of chip 1158 forms at least part of the floor of vessel 1220. A cell-receiving area 1181 is formed in vessel 1220, adjacent top surface 1163. An electrolyte-receiving space 1181 is located over cell-receiving area 1184.

A removable cover 1216 is operatively positionable over electrolyte-receiving space 1181 (see FIG. 17). Cover 1216 is not shown in FIGS. 15 and 16. Cover 1216 includes a counter electrode 1174 attached to and supported by a body 1218, such that counter electrode 1174 faces chip 1158 and each sampling electrode 1156 thereof.

Isolation device 1190 may have a series of electrical connectors, such as pins 1221, attached to housing 1212 (see FIGS. 15 and 16). The connectors are used to electrically connect electronics of isolation device 1190 (such as chip electronics and/or other (non-chip) device electronics) to other components of the control circuit and/or to a source of electrical power.

FIG. 17 shows a fragmentary sectional view of isolation device 1290 taken through one sampling electrode 1256 and its corresponding well 1262. Using at least one voltage source, an individually controllable voltage can be applied to each sampling electrode 1256. In other words, the voltage is applied between counter electrode 1274, indicated by electric potential V1, and the sampling electrode 1256, indicated by electric potential V2, where the difference between V2 and V1 is the applied voltage. Accordingly, application of a positive voltage to sampling electrode 1256 makes the sampling electrode a positive electrode or anode, while application of a negative voltage to sampling electrode 1256 makes the sampling electrode a negative electrode or cathode.

Copies of a tag 1166 are supported by and attached to chip 1158 over electrode 1156 in well 1162. More specifically, each copy of tag 1166 is connected to electrode 1156 via a porous layer 1195 located on a top surface of electrode 1156. Each copy of tag 1166 may be covalently attached to porous layer 1195 or associated with the porous layer noncovalently. The copies of each different tag 1166 may be synthesized in situ on chip 1158, such as in situ on a respective porous layer 1195 in well 1162, or may be synthesized separately and then deposited in well 1162 of chip 1158. In other examples, copies of tag 1166 may be supported by chip 1158 but are not connected to the chip (see Example 4).

Tag 1166 includes an identifier 1168 covalently linked to a capturing agent 1170, where each of identifier 1168 and capturing agent 1170 includes a series of nucleotides. ("UMI" is an acronym for unique molecular identifier.) Here, capturing agent 1170 includes a series of deoxythymidine nucleotides (i.e., TTT . . . TTT) of any suitable length, such as at least 8, 10, 12, or more nucleotides. In other examples, the capturing agent may include one or more deoxyuridine nucleotides, such as an oligo(dU) sequence of at least 8, 10, 12, or more nucleotides. In yet other examples, the capturing agent may include a combination of deoxythymidine and deoxyuridine residues. In still other examples, the capturing agent may include a degenerate nucleotide sequence, (N)x, extending to the 3'-end of the tag, where N is a mix of A, C, G, and T (or U), and x is at least 3, 4, 5, 6, 7, or 8.

Chip 1158 has a series of layers each oriented parallel to top surface 1163, as explained above in Example 2. These layers may include a substrate 1197, dielectric layer 1165, and a cell adhesion layer 1222. Cell adhesion layer 1222 may be located over and/or on dielectric layer 1165. The cell adhesion layer 1222 may include any suitable material to encourage overlying cells to adhere to top surface 1163 of chip 1158. For example, the cell adhesion layer may be a coating including a polypeptide, such as an Ig superfamily cell adhesion molecule, integrin, cadherin, selectin, polylysine, or the like.

Example 4

Isolation Device with Bead Array

Figure 18:
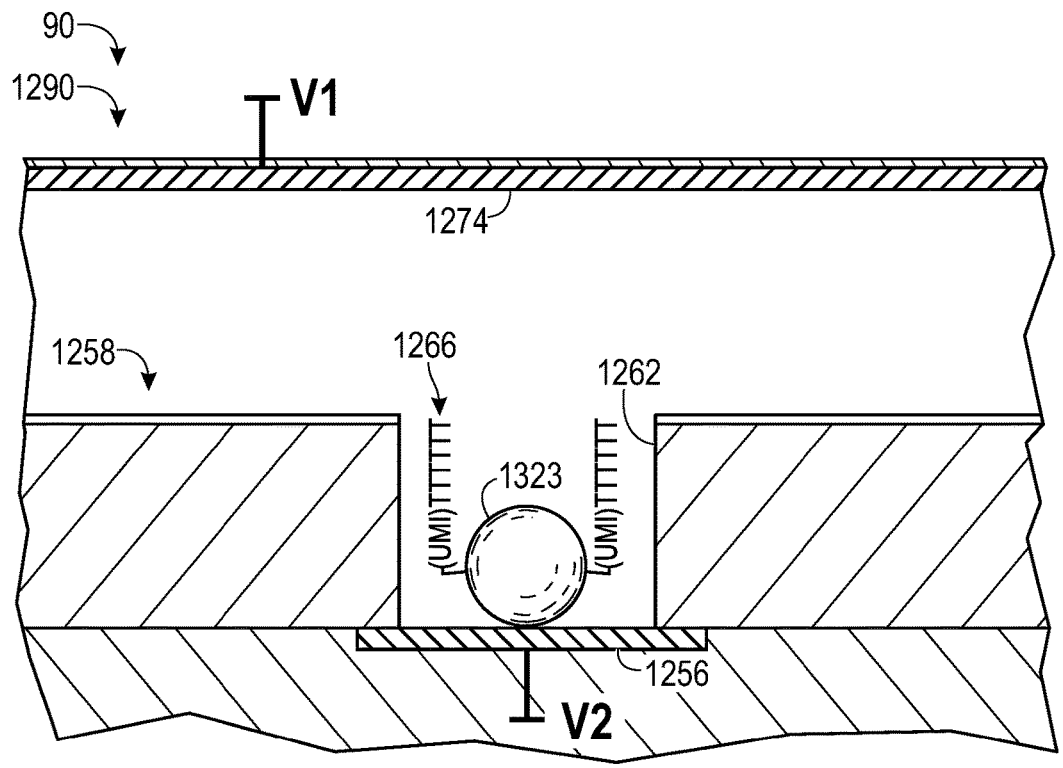
FIG. 18 is fragmentary sectional view of another exemplary isolation device, taken as in FIG. 17, but with the well containing a removable bead to which a tag of a tag array is attached.

This example describes an exemplary embodiment, isolation device 1290, of isolation device 90 for the systems and methods of the present disclosure; see FIG. 18 (also see FIG. 2).

Isolation device 1290 is structurally similar to isolation device 1190, except that each tag 1266 is supported by a chip 1258 but not connected to the chip. Instead, copies of the tag 1266 are connected to a bead 1323, which is located at least partially in a well 1262, optionally supported on the top surface of electrode 1256. In the depicted embodiment, the diameter of bead 1323 is less than the depth of the well, such that the bead is completely inside the well. In other examples, at least two beads connected to the same tag or different tags may be located in well 1262. In other examples, a portion of the bead may protrude from the well. Beads of any suitable shape may be used. Beads may be advantageous because tags 1266 can be synthesized on the beads separately from the chip, and then individual beads each carrying a different tag 1266 may be placed into different wells 1262. Moreover, synthesis of tags 1266 may be performed more easily on beads, such as with a split-and-pool approach.

Example 5

Method of Sampling RNA From Cells of a Tissue Section

This example describes exemplary steps that may be performed, and configurations that may be generated, in a method of sampling RNA from cells of a tissue section; see FIGS. 19-27.

Figure 19:
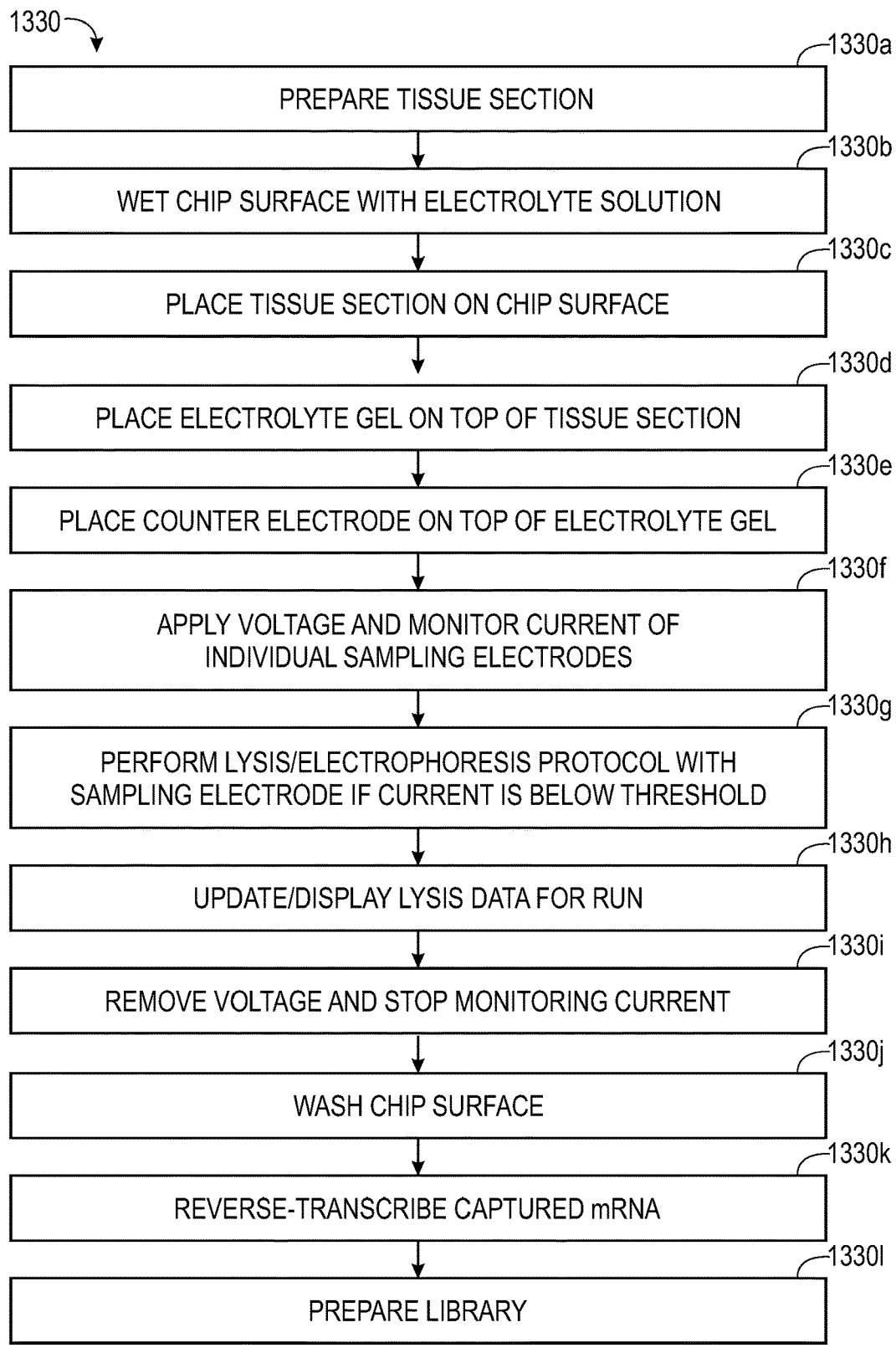
FIG. 19 is a flowchart listing exemplary steps of an exemplary method of sampling nucleic acids from cells of a tissue section.

FIG. 19 show a flowchart listing steps of an exemplary method 1330 of sampling cells of a tissue section for RNA. Method 1330 is an example of method 130 of FIG. 3 described above in Section I. Steps 1330a-1330l listed in FIG. 19 may be performed in any suitable order and combination, using any other suitable aspects of the systems and methods of the present disclosure.

Figure 20:
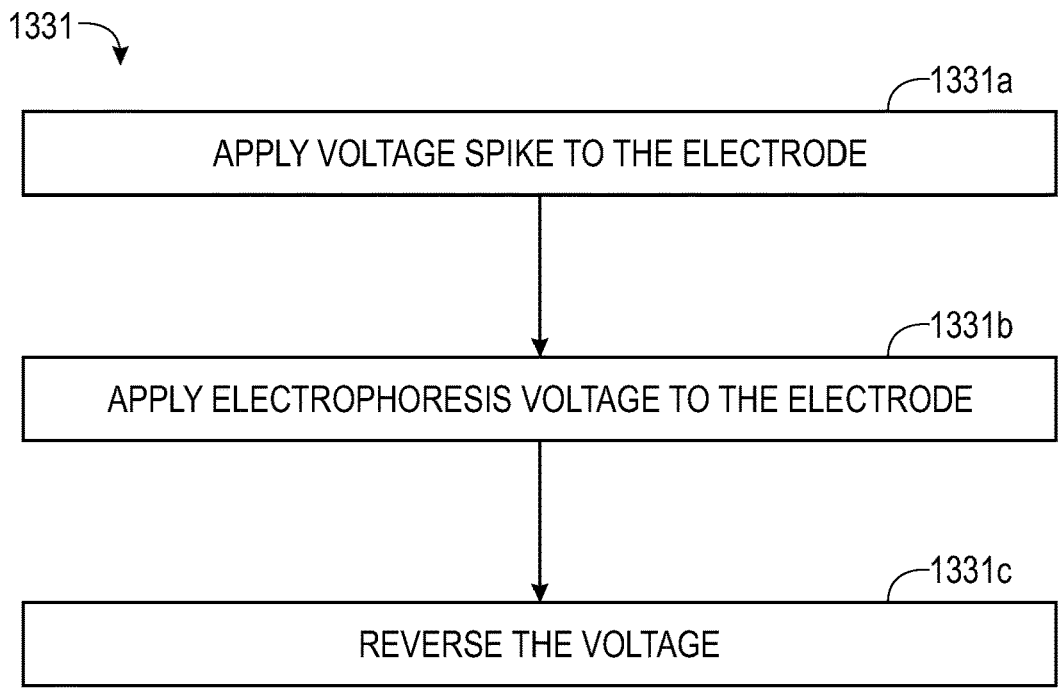
FIG. 20 is a flowchart listing exemplary steps of an exemplary lysis/electrophoresis routine that may be performed within the method of FIG. 19.

FIG. 20 shows a flowchart listing steps of an exemplary lysis/electrophoresis protocol 1331 that may be performed as step 1330g within method 1330 of FIG. 19. Steps 1331a-1331c listed in FIG. 20 may be performed in any suitable order and combination, using any other suitable aspects of the systems and methods of the present disclosure.

Figure 21:
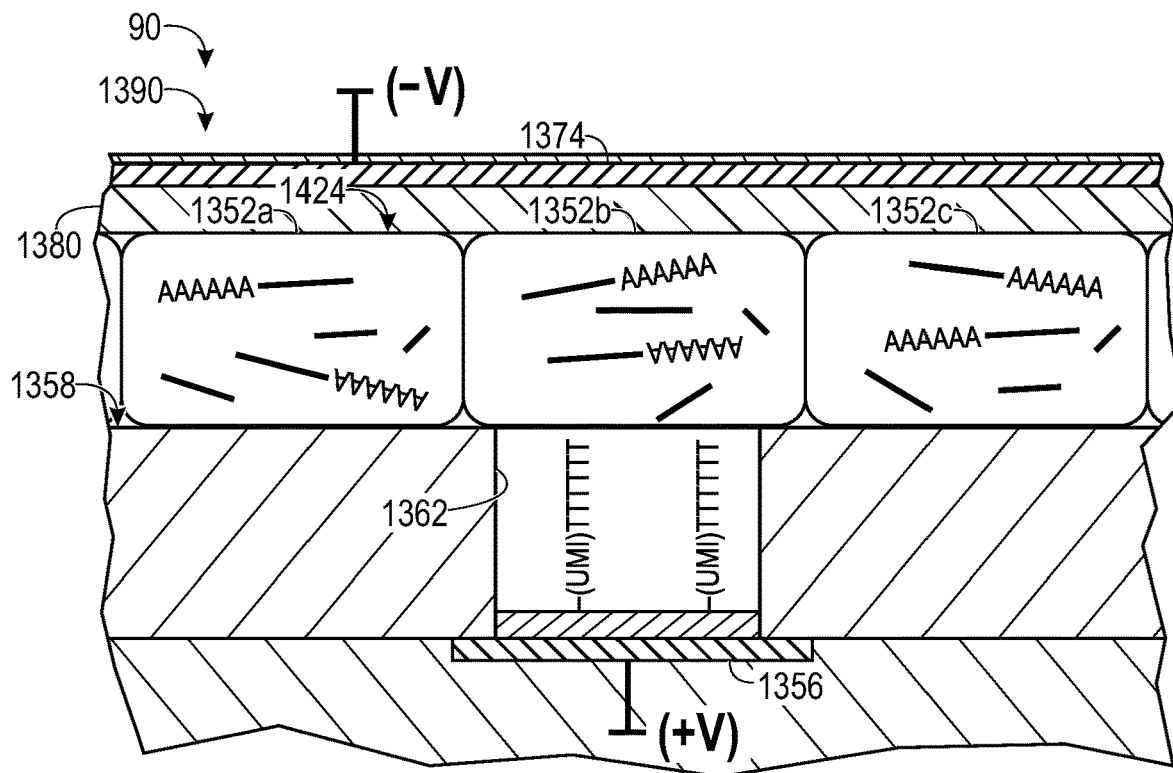
FIG. 21 is a schematic fragmentary sectional view of an exemplary configuration of an exemplary isolation device produced after performing the first five steps of the method of FIG. 19.

FIG. 21 shows a fragmentary sectional view of an exemplary configuration of an embodiment (isolation device 1390) of isolation device 90 (also see FIG. 2). The configuration shown here may represent step 1330f of method 1330 of FIG. 19. A tissue section 1424 composed of a layer of cells, including illustrative cells 1352a, 1352b, and 1352c, is sandwiched between an electrolyte gel 1380 and a surface of chip 1358 of isolation device 1390. Tissue section 1424 adheres to the chip surface. Electrolyte gel 1380 allows application of uniform top-to-bottom pressure and improves adhesion of tissue section 1424 to the surface of chip 1358. A counter electrode 1374 may be in physical contact with electrolyte gel 1380, or a layer of electrolyte liquid may be located between electrolyte gel 1380 and counter electrode 1374. A sampling electrode 1356 and a corresponding well 1362 are aligned with illustrative cell 1352b.

FIGS. 22-27 show exemplary configurations that may be produced with isolation device 1390 of FIG. 21 during performance of method 1330 of FIG. 19.

Figure 22:
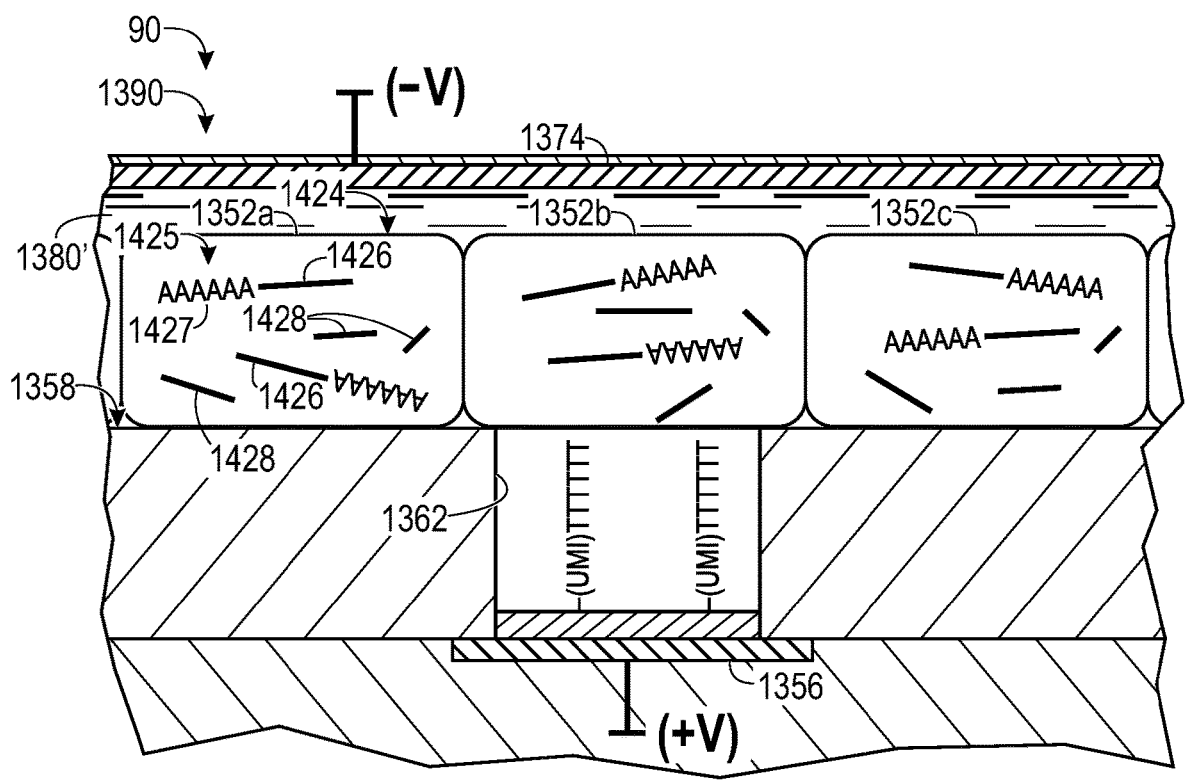
FIGS. 22-27 are schematic fragmentary sectional views of exemplary configurations that may be produced with the isolation device of FIG. 21 during performance of the method of FIG. 19, except with an electrolyte liquid rather than an electrolyte gel placed on top of the tissue section.

FIG. 22 shows isolation device 1390 and tissue section 1424 in the same configuration as FIG. 21, except with an electrolyte liquid 1380', rather than an electrolyte gel, located between tissue section 1424 and counter electrode 1374. Each cell 1352a-1352c contains nucleic acids 1425, including messenger RNA molecules 1426 each having a poly(A) tail 1427. Each cell also contains other nucleic acids 1428, such as RNA having no poly(A) tail or DNA (double-stranded or single-stranded). Cell 1352b is aligned with sampling electrode 1356 and located over the mouth of the corresponding well 1362. The plasma membrane of cell 1352b is in very close proximity to the top surface of chip 1358 around well 1362, such that cell 1352b reduces the electrical current measured at electrode 1356 in response to application of a positive test voltage, indicated by "(+V)" and "(−V)" at sampling electrode 1356 and counter electrode 1374, respectively. More specifically, the measured electric current is lower than without cell 1352b or lower than with a greater separation between cell 1352b and the top surface of chip 1358 and is less than a threshold.

Figure 23:
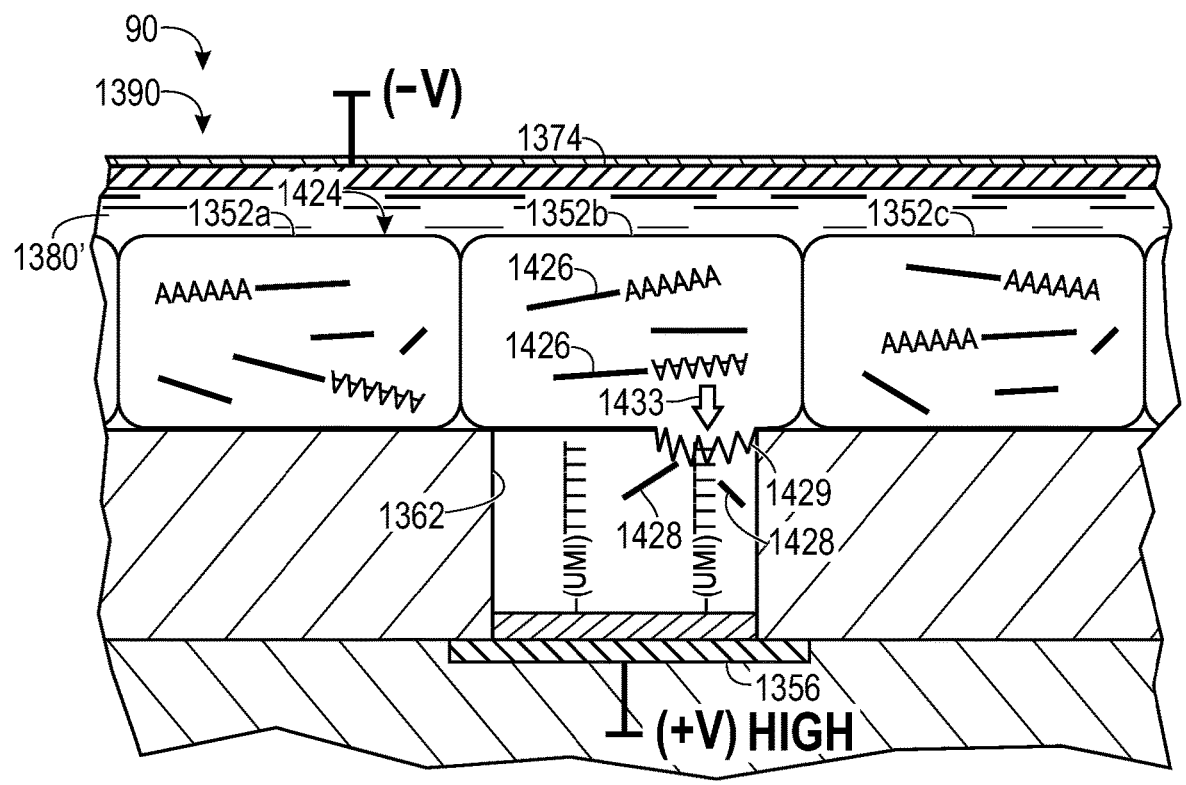

FIG. 23 schematically illustrates application of a lysis voltage to sampling electrode 1356, indicated as "(+V) High" below the sampling electrode. The lysis voltage is rupturing the plasma membrane of cell 1352b, indicated at 1429, and nucleic acids 1428 are being released from cell 1352b and traveling toward electrode 1356, indicated by a motion arrow at 1433. The greatest electric potential and induced pressure is located near a narrowing of the conductor (electrolyte) between the lip of the well and cell 1352b. Electric potential dissipates rapidly with distance along the surface of chip 1358 from well 1362. Accordingly, only the plasma membrane (and/or wall) of a cell(s) very near to well 1362 is ruptured.

Figure 24:
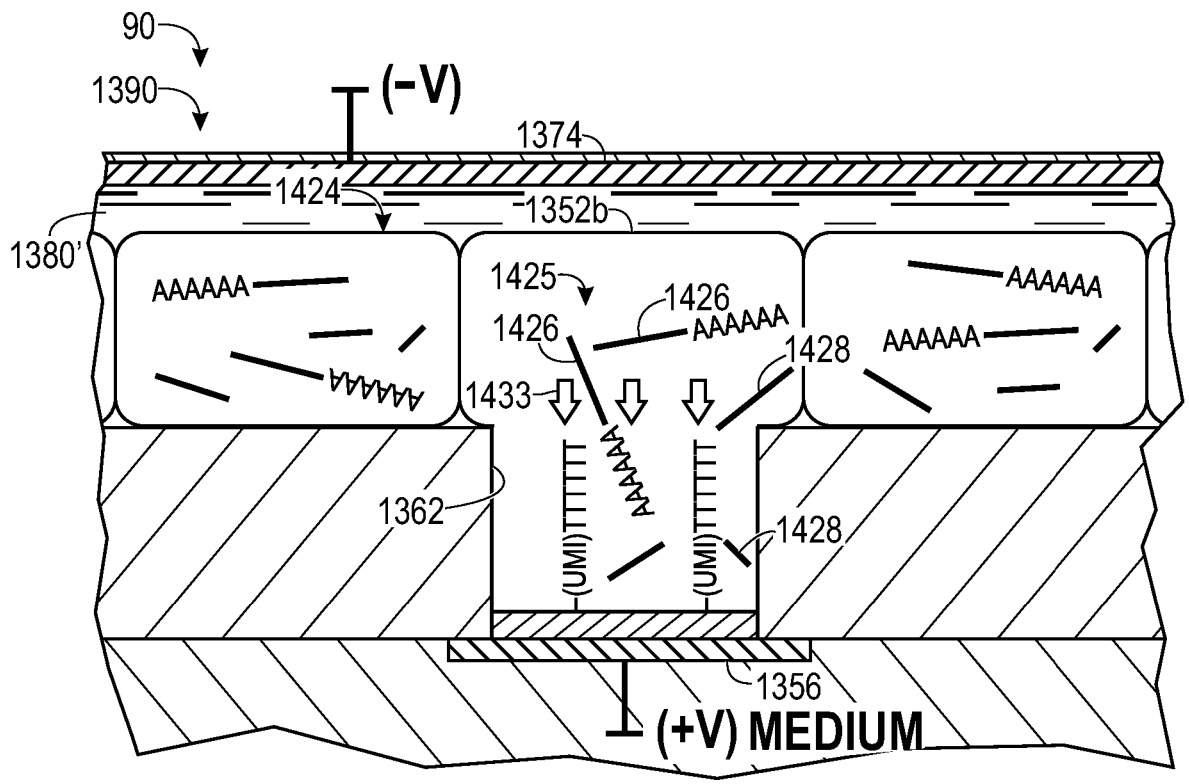

FIG. 24 schematically illustrates application of an electrophoresis voltage to sampling electrode 1356, indicated as "(+V) Medium" below the sampling electrode. The plasma membrane of cell 1352b has been ruptured by the previously applied lysis voltage and does not significantly obstruct travel of nucleic acids 1425 into well 1362 and toward sampling electrode 1356, indicated by a set of motion arrows at 1433. Electric potential dissipates quickly with distance along chip 1358 from well 1362. Accordingly, only nucleic acids from cell 1352b are driven electrophoretically into well 1362.

Figure 25:
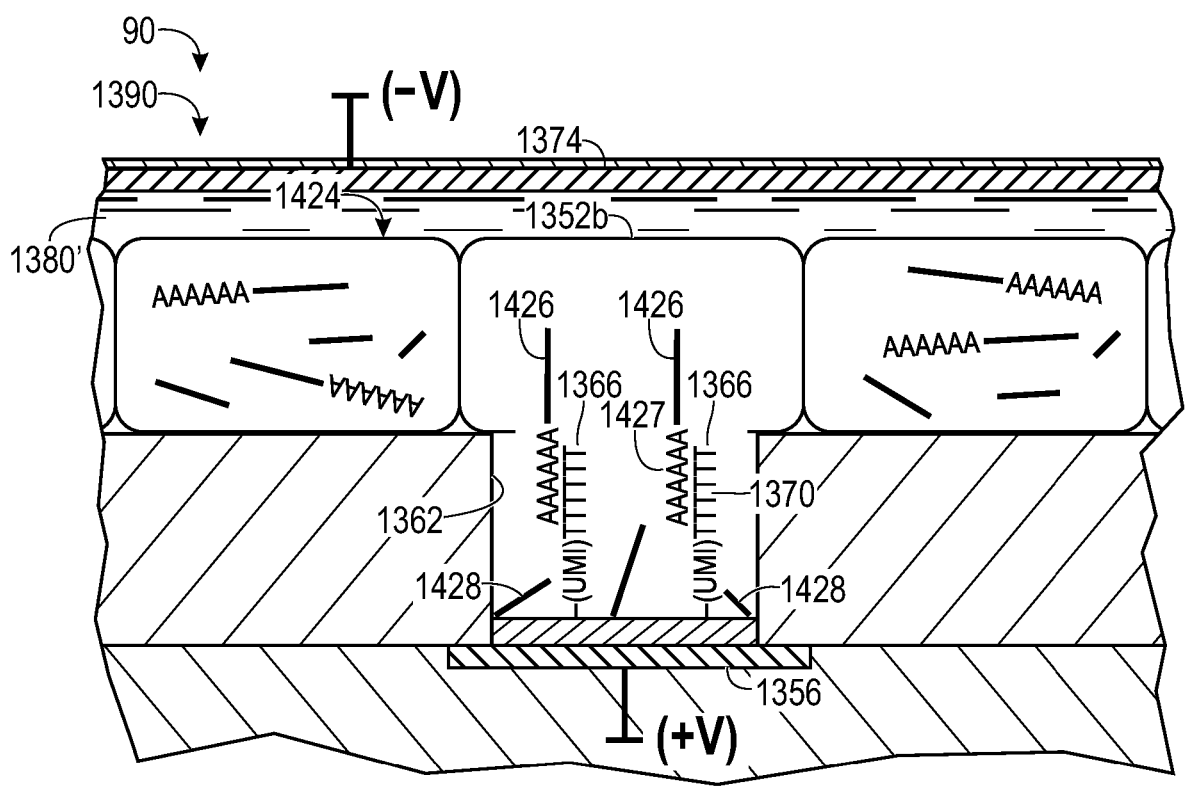

FIG. 25 schematically illustrates a configuration produced at the end of the electrophoresis phase, which is indicated by "(+V)" below sampling electrode 1356. Messenger RNA molecules 1426 have entered well 1362 and are hybridized with copies of tag 1366. More specifically, the poly(A) tail 1427 of messenger RNA molecules 1426 is hybridized with an oligo(dT) capturing agent 1370 of tag 1366. Other nucleic acids 1428 having no poly(A) tail have approached sampling electrode 1356 but are not hybridized to capturing agent 1370.

Figure 26:
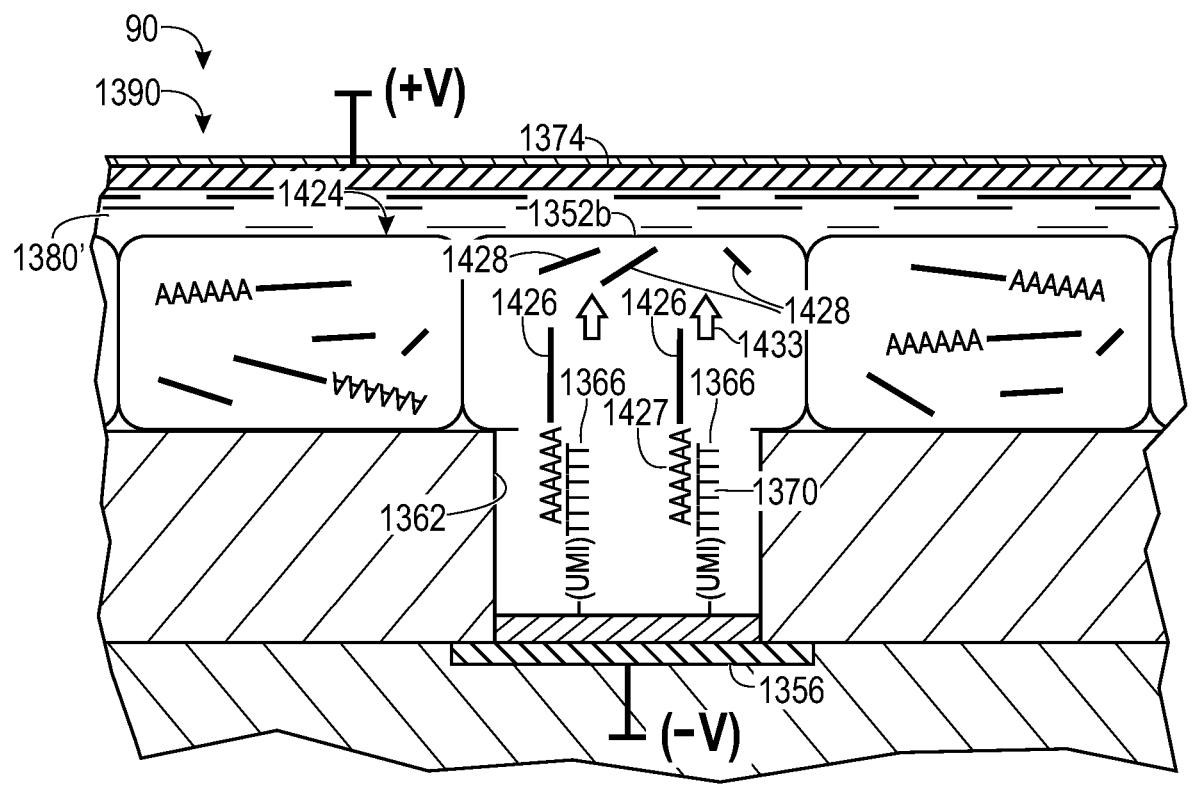

FIG. 26 schematically illustrates a configuration produced during a reverse electrophoresis phase. The reverse electrophoresis phase is driven by reversing the polarity of the voltage applied to sampling electrode 1356, as indicated by "(−V)" instead of "(+V)" below sampling electrode 1356. Messenger RNA molecules 1426 remain captured by hybridization to immobilized capturing agent 1370 of tag 1366. In contrast, unbound other nucleic acids 1428 are free to travel out of well 1362 in response to the reversed voltage, which helps to purify the captured messenger RNA molecules 1426 by separating them from other nucleic acids 1428.

Figure 27:
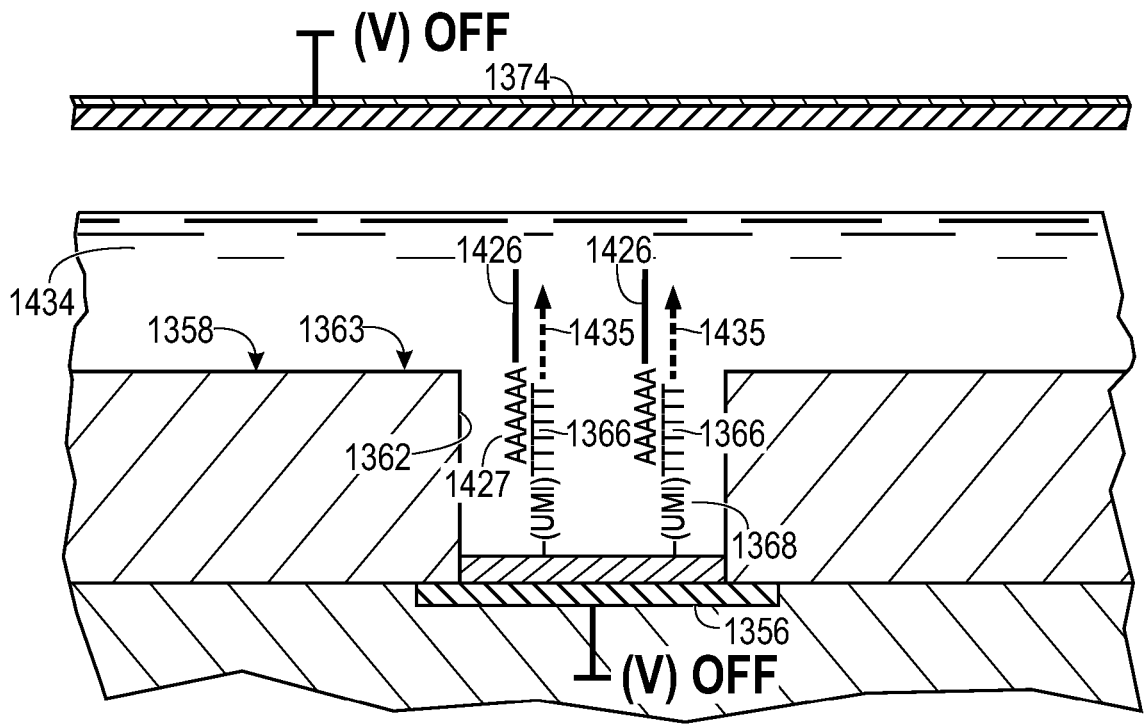

FIG. 27 schematically illustrates a configuration produced after voltage application has been stopped and tissue section 1424 removed (compare with FIG. 26). The top surface 1363 of chip 1358 has been washed, to remove cell debris and any unbound cell components. A reverse-transcription reaction mixture 1434 has been placed onto top surface 1363 of chip 1358, such that reaction mixture 1434 enters each well 1362 of chip 1358. Reaction mixture 1434 includes a reverse transcriptase and dNTPs. The reverse transcriptase catalyzes extension of hybridized copies of tag 1366 to form complementary DNA molecules, indicated at 1435, using tag 1366 as a primer and hybridized messenger RNA molecules 1426 as templates. After completion of the reverse transcription reaction, the resulting complementary DNA molecules can be released from chip 1358, pooled, and processed collectively to produce a library for sequencing. Library members originating from the same well 1362, and thus the same cell or group of cells, can be identified after pooling as containing the unique identifier 1368 for that well (or the complement of the unique identifier).

Example 6

Method and Device for Sampling Isolated Cells

This example describes an exemplary method and an exemplary embodiment (isolation device 1490) of isolation device 90 for sampling nucleic acids from single cells and/or small cell clusters that are not physically connected to one another; see FIGS. 28-36.

Figure 28:
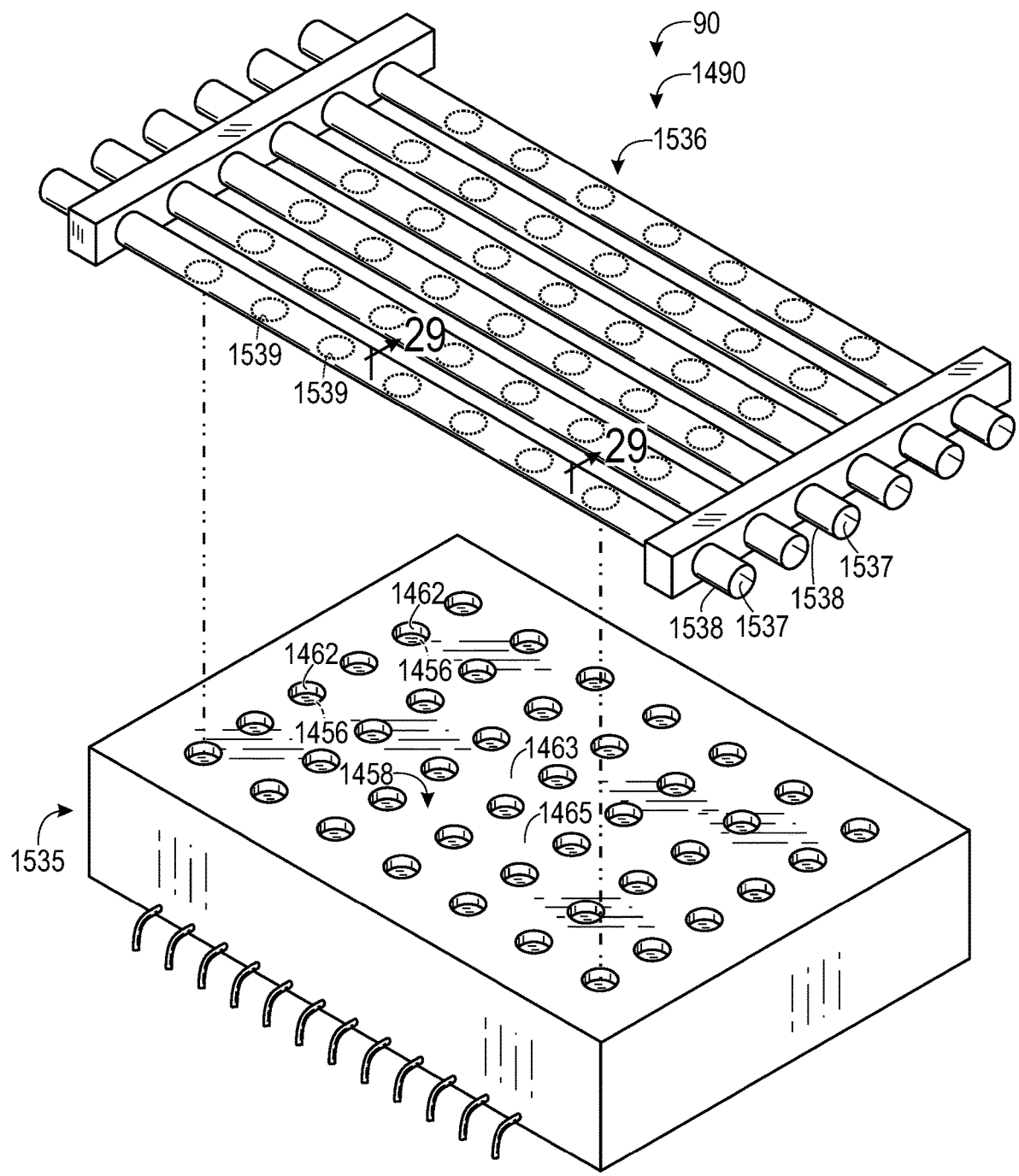
FIG. 28 is an exploded fragmentary isometric view of an exemplary isolation device for sampling nucleic acids from isolated cells instead of cells of a tissue section, where the isolation device has a series of capillary tubes each communicating laterally with a different row of wells of the isolation device.

FIG. 28 shows an exploded view of isolation device 1490. A base 1535 of isolation device 1490 includes a chip 1458 having an array of sampling electrodes 1456 aligned with an array of wells 1462. Chip 1458 may have any suitable combination of features and structures described elsewhere herein, including a top surface 1463 and a dielectric layer 1465.

A channel-forming assembly 1536 is attached to top surface 1463 of chip 1458. Channel-forming assembly 1536 has a plurality of channels 1537 provided by a corresponding number of capillary tubes 1538. Each capillary tube 1538 has a series of lateral openings 1539 for fluid communication with a series of wells 1462 of chip 1458. Capillary tube 1538 form a fluid-tight seal with each well 1462 of a row of wells of chip 1458.

FIGS. 29-34 show exemplary configurations produced by operation of isolation device 1490 during performance of a sampling method according to FIG. 3. Isolation device 1490 is shown as fragmentary and sectional, with the views taken through three wells 1462 arranged along one of the rows of isolation device 1490 and the corresponding overlying capillary tube 1538. The configurations shown here conceptually correspond to those shown above in FIGS. 22-27 in Example 5 for isolation device 1390 and a tissue section instead of isolated cells.

Figure 29:
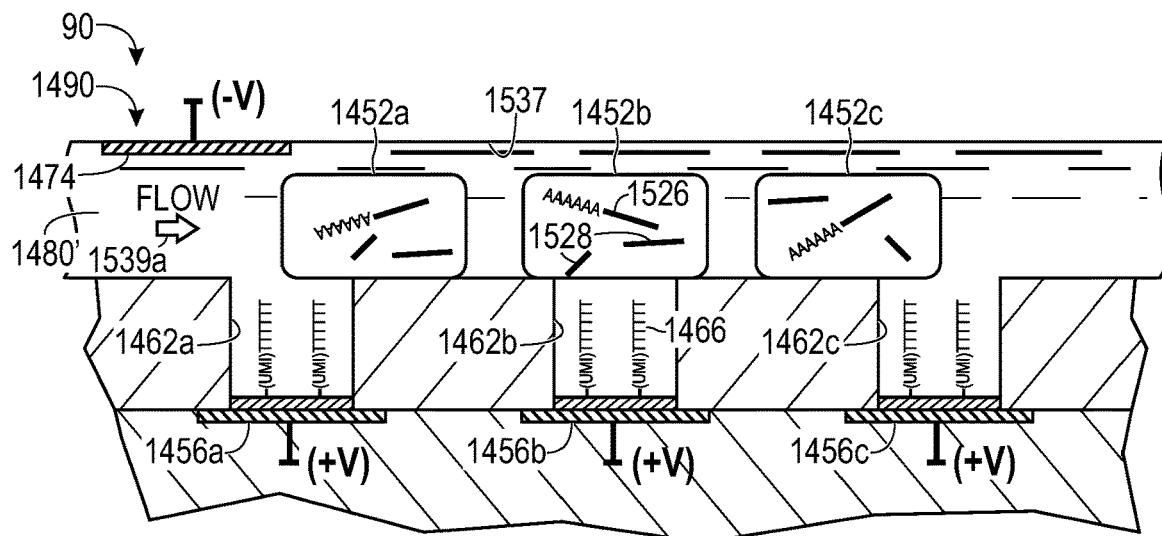
FIGS. 29-34 are schematic fragmentary sectional views of the isolation device of FIG. 28, taken generally along line 29-29 of FIG. 28 and illustrating a series of exemplary configurations that may be produced with the isolation device of FIG. 28 during performance of aspects of the sampling method of FIG. 3.

FIG. 29 shows cells 1452*a*-*c* in an electrolyte liquid 1480' being introduced into channel 1537 by fluid flow, indicated at 1539*a*. Cell 1452*b* is centered over sampling electrode 1456*b* and a corresponding well 1462*b*, but cells 1452*a* and 1452*c* are not centered over sampling electrodes 1456*a*, 1456*c* and wells 1462*a*, 1462*c*. A test voltage can be applied to each sampling electrode 1456*a*-*c* with the aid of a counter electrode 1474 located in channel 1537. Measured electric current produced by the test voltage varies among sampling electrodes 1456*a*-*c*, with sampling electrode 1456*b* having a lower electric current than sampling electrodes 1456*a* and 1456*c*.

Figure 30:
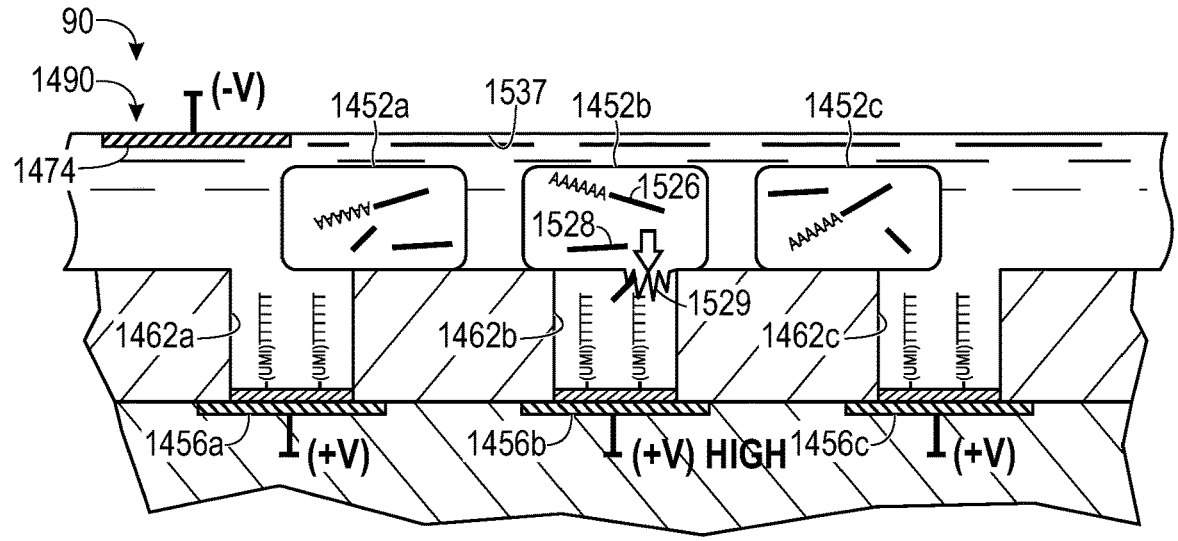

FIG. 30 shows a lysis voltage "(+V) High" being applied to sampling electrode 1456*b* in response to the lower electric current measured for the sampling electrode. The membrane of cell 1452*b* is being ruptured locally, indicated at 1529.

Figure 31:
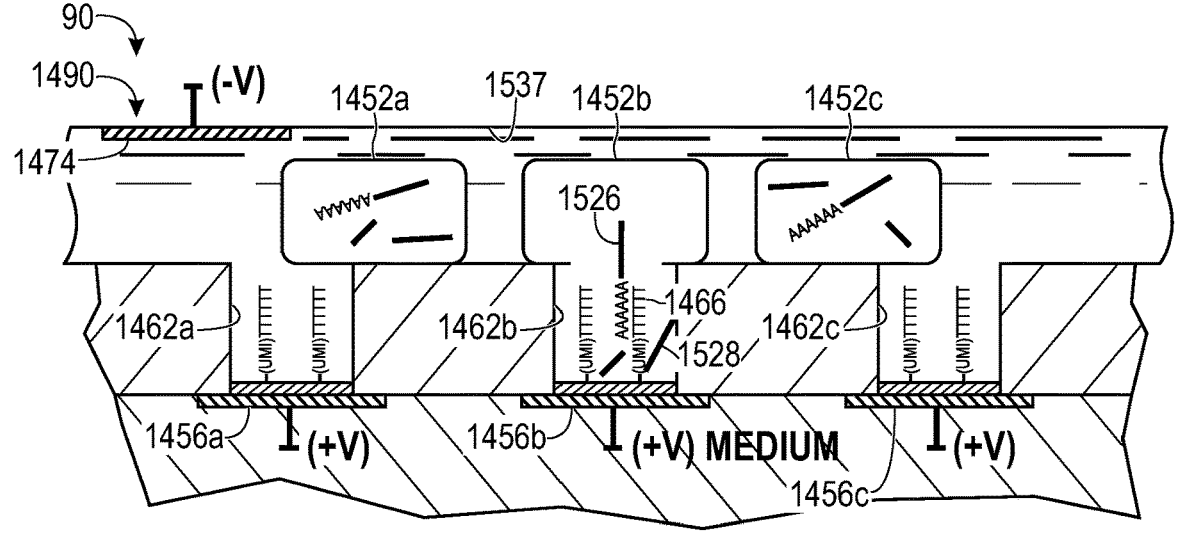

FIG. 31 shows an electrophoresis voltage "(+V) Medium" being applied to sampling electrode 1456*b* after application of the lysis voltage. Nucleic acids including a messenger RNA molecule 1526 and other nucleic acids 1528 are being driven into well 1462*b*, and messenger RNA molecule 1526 has hybridized with a tag 1466.

Figure 32:
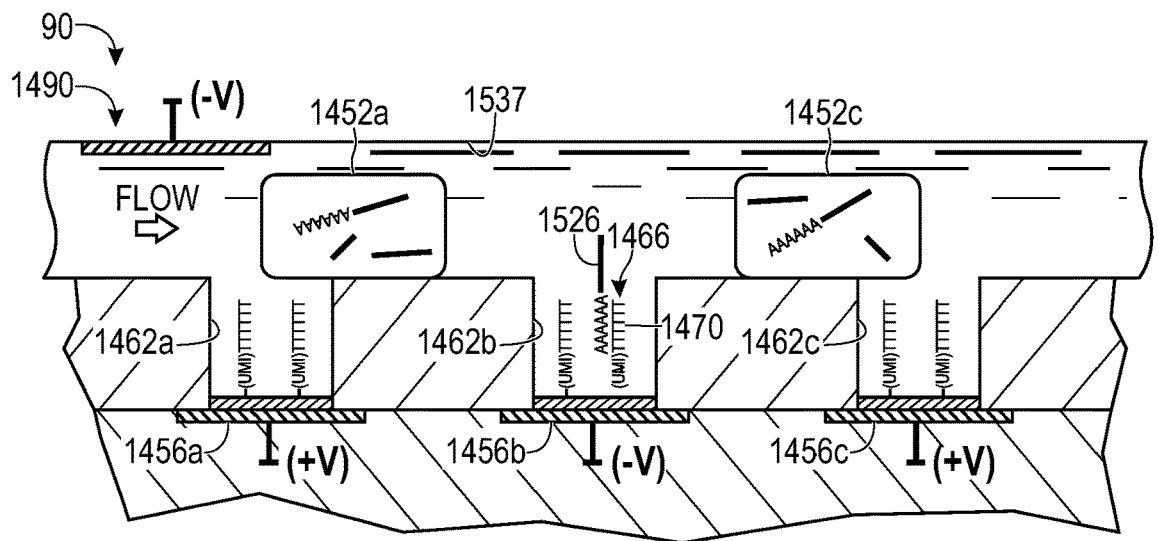

FIG. 32 shows well 1462*b* after application of a reverse voltage to well 1462*b*, to remove nucleic acids not captured by capturing agent 1470 of tag 1466.

Figure 33:
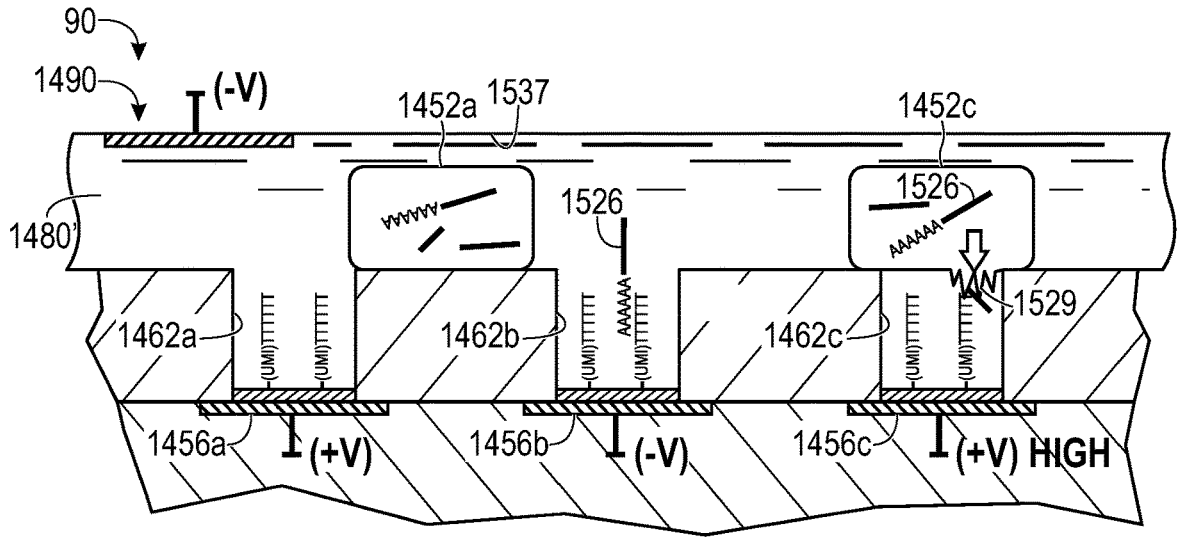

FIG. 33 shows the result of further flow of electrolyte liquid 1480 along channel 1537, such that cells 1452*a* and 1452*c* having advanced (compare with FIG. 33). Cell 1452*c* in now centered on well 1462*c*, which produced a lower measured electric current for electrode 1456*c*. As a result, a lysis voltage "(+V) High" is being applied to electrode 1456*c*, which produces local rupture of the cell membrane, indicated at 1529.

Figure 34:
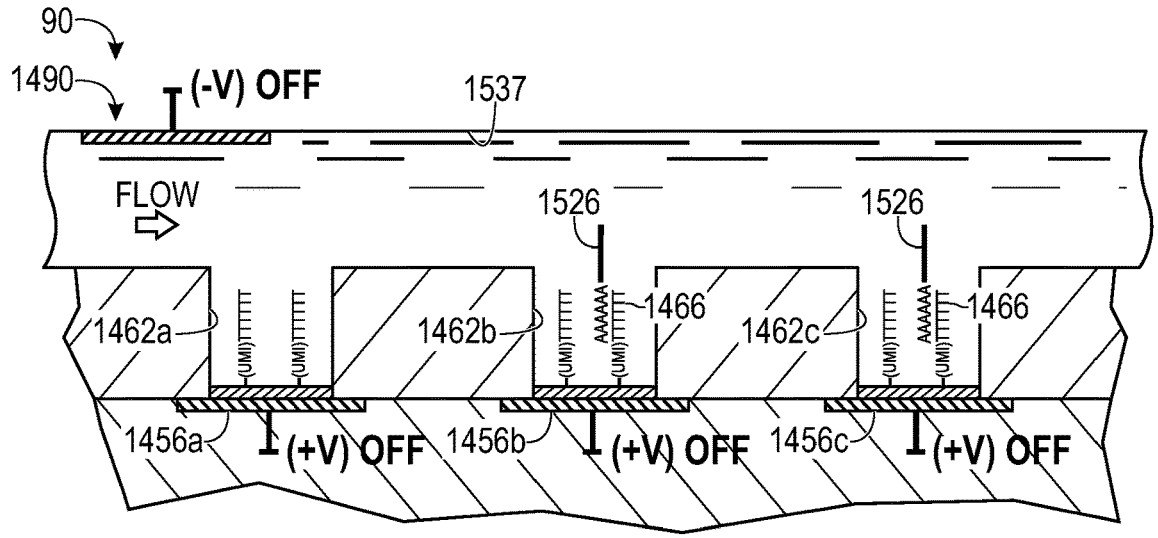

FIG. 34 shows a configuration produced after mRNA molecules 1526 have been captured in each of wells 1462*b* and 1462*c*. Further flow of electrolyte liquid or a washing solution removes unbound cell components and non-lysed cells.

Figure 35:
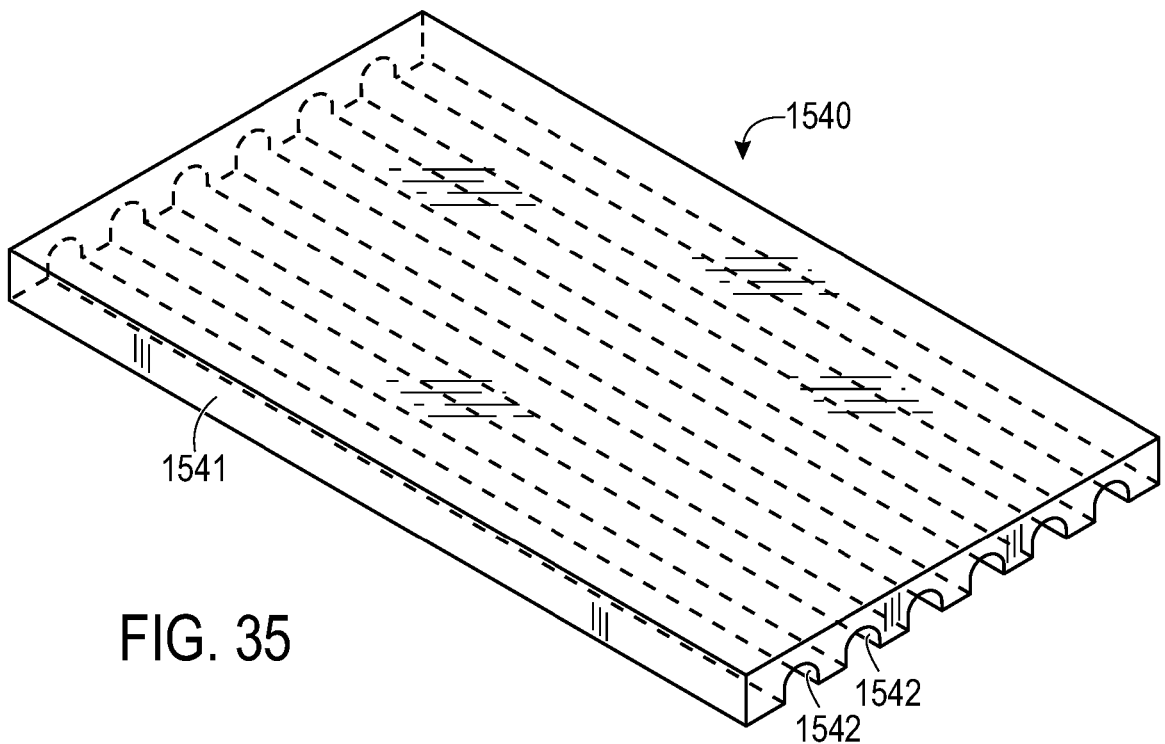
FIG. 35 is an isometric view of an exemplary channel-forming member that can be bonded to the top surface of a chip of the isolation device of FIG. 28, to replace the series of capillary tubes of FIG. 28.

FIG. 35 shows an exemplary channel-forming member 1540 that can be bonded to the top surface of chip 1458 in place of channel-forming assembly 1536 (compare with FIG. 28). Channel-forming member 1540 may be a sheet 1541 defining channels 1542 in a bottom surface of the sheet, with the channels having a spacing from one another matching the spacing between rows of wells 1462 of chip 1458.

Figure 36:
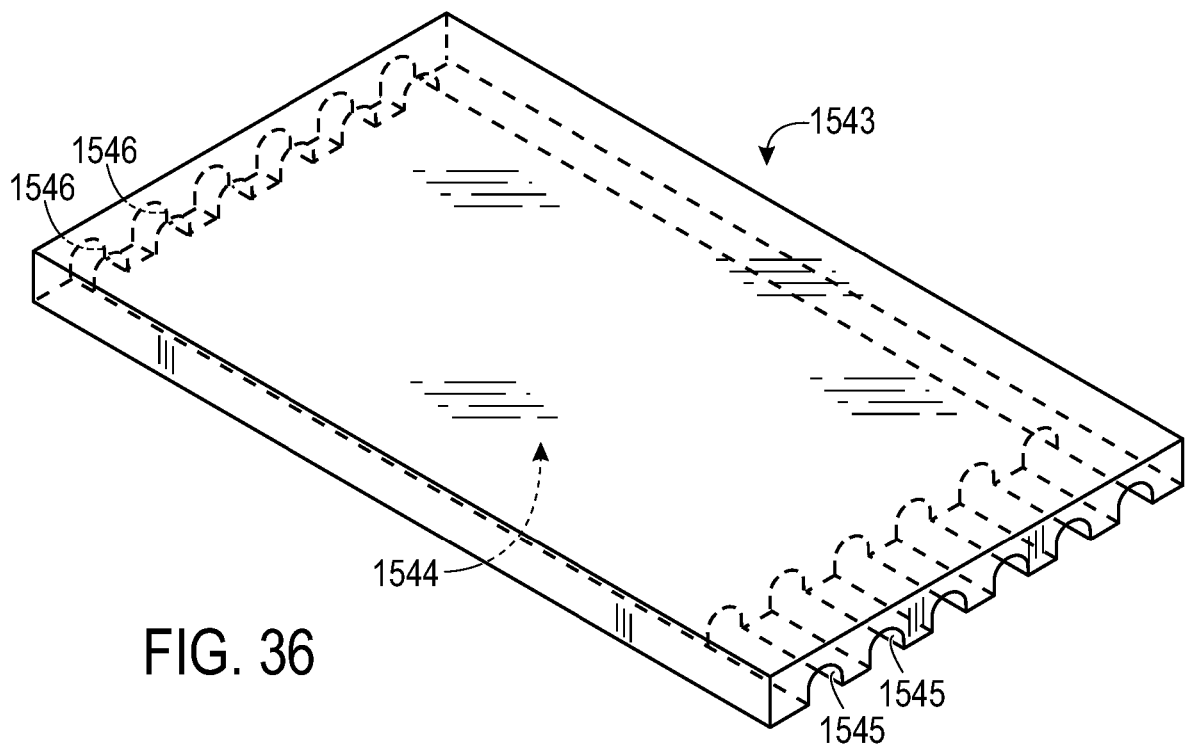
FIG. 36 is an isometric view of a chamber-forming member than can be bonded to the top surface of a chip of the isolation device of FIG. 28, to replace the series of capillary tubes.

FIG. 36 shows an exemplary chamber-forming member 1543 that can be bonded to the top surface of chip 1458 in place of channel-forming assembly 1536 (compare with FIG. 28). Chamber-forming member 1543 may be a sheet defining (i) a recess forming the side walls and ceiling of a chamber 1544, (ii) one or more inlet channels 1545 to carry cells in electrolyte to chamber 1544, and (iii) one or more outlet channels 1546 to carry cells in electrolyte from chamber 1544.

Example 7

DNA Capture and Tagging

Figure 37:
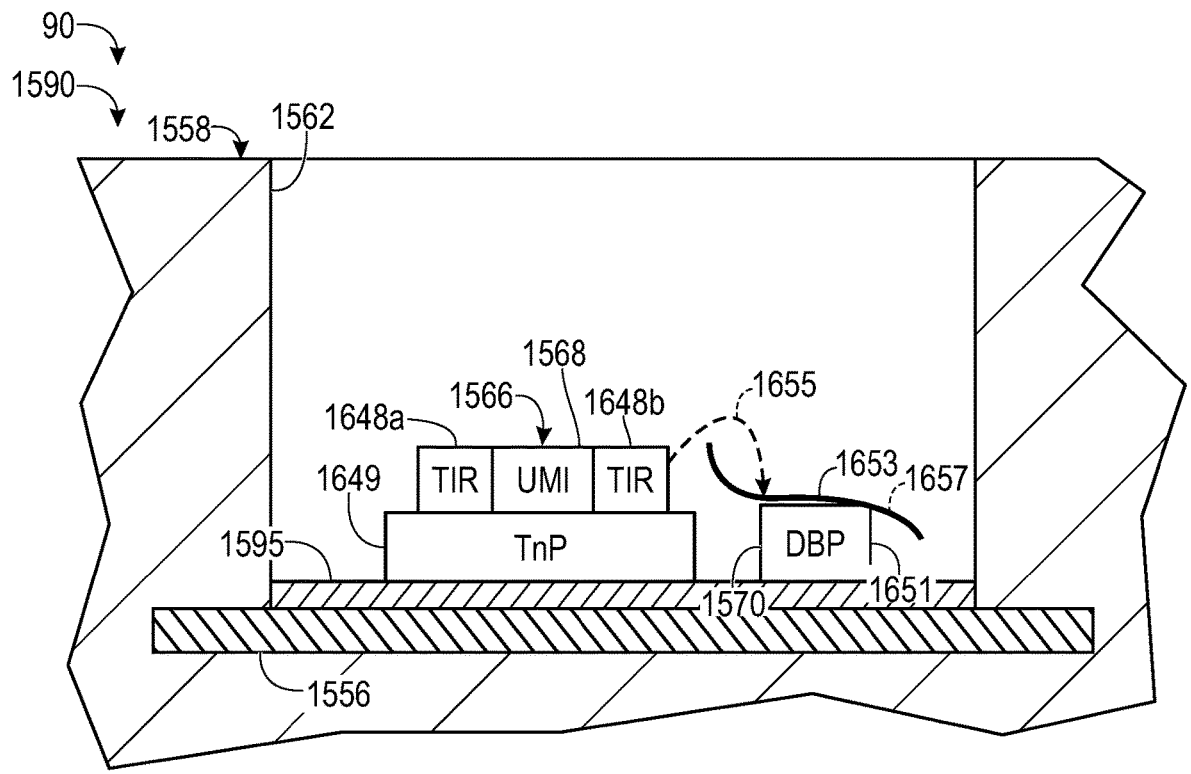
FIGS. 37 and 38 are schematic fragmentary sectional views of an embodiment of the collection device of FIG. 3, taken through a well and corresponding sampling electrode and illustrating an exemplary configuration of electrode-associated reagents for capturing and tagging DNA sequences released from an overlying cell.
Figure 38:
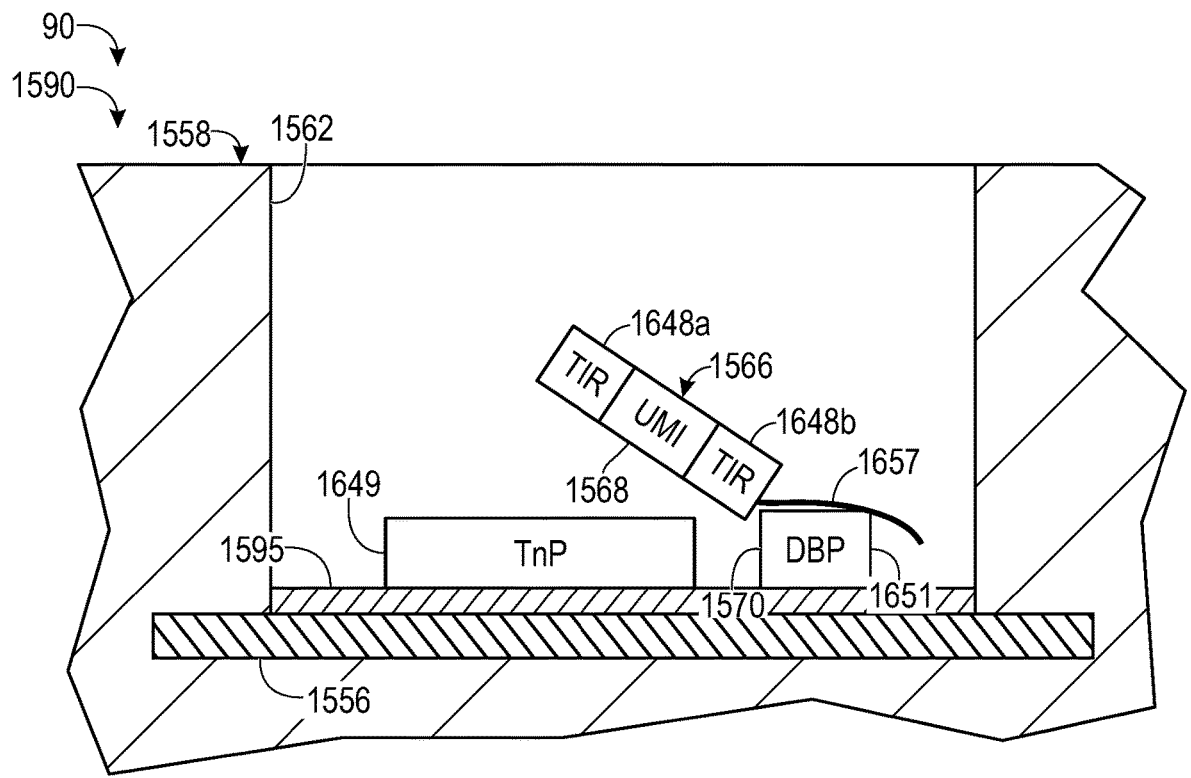

This example describes an exemplary method, system, and isolation device 1590 for sampling DNA from cells; see FIGS. 37 and 38.

Isolation device 1590 may have any suitable combination of elements and features described for isolation devices elsewhere herein. For example, the isolation device may include a chip 1558 having an array of sampling electrodes, an aligned well array, and an aligned tag array (only one sampling electrode 1556, well 1562, and tag 1566 are shown here). Each tag 1566 has an identifier 1568 that is unique to the tag array, as described above for similar chips and isolation devices. The tag 1566 also has at least one transposase recognition sequence, such as a pair of terminal inverted repeats (1648a, 1648b) (TIRs). Terminal inverted repeats 1648a, 1648b are associated with a transposase 1649 (TnP), which is connected to sampling electrode 1556 via a porous layer 1595.

A capturing agent 1570 in the form of a DNA-binding protein 1651 (DBP) is connected to electrode 1556 via porous layer 1595. DNA-binding protein 1651 may bind DNA duplexes, such as DNA duplex 1653, without substantial sequence specificity. Before or after DNA duplex 1653 has been bound by DNA-binding protein 1651, transposase 1649 covalently attaches, indicated at 1655, tag 1566 to a fragment 1657 of DNA duplex 1653 via tagmentation (compare FIGS. 37 and 38). In other examples, DNA-binding protein 1651 may be omitted and transposase 1649 may act as a capturing agent 1570.

Example 8

Protein/Analyte Capture and Associated Tagging

This example describes an exemplary system and method for sampling a net positively-charged or negatively-charged protein (or other charged analyte) from cells. A tag array may be formed in alignment with an electrode array of sampling electrodes and an optional well array, as described above. Copies of a capturing agent (i.e., a first binding partner), such as an antibody or other specific binding partner for the protein/analyte, may be immobilized in alignment with each sampling electrode of the electrode array (e.g., in a corresponding well aligned with the sampling electrode). The protein/analyte may be released from cells by electrical lysis, as described elsewhere herein, and driven by electrophoresis of suitable polarity to the copies of the first binding partner aligned with corresponding sampling electrodes. The immobilized first binding partner binds to (captures) the protein or other analyte, and then the electrophoresis polarity may be reversed to remove unbound cell components by reverse electrophoresis. After sampling has been completed at a desired number of sampling electrodes, further processing may be performed in parallel with the captured protein/analyte. A second binding partner for the protein/analyte may be placed on the tag array. The second binding partner may be labeled with an oligonucleotide. The first and second binding partners may be configured to bind the protein/analyte non-competitively, such that both can be bound to the same copies of the protein/analyte at the same time. The proximity of unique tags and the oligonucleotide to one another at individual positions of the array then may be utilized to perform proximity-dependent ligation or extension. In proximity-dependent ligation, the tags and the oligonucleotide are ligated to one another, optionally with the aid of a splint oligo. In proximity-dependent extension, the tags and/or the oligonucleotide are extended while hybridized to one another. With either approach, the resultant ligation products or extension products may be pooled and used to prepare a library for sequencing.

IV. SELECTED ASPECTS

This section describes selected aspects of the present disclosure as a series of indexed paragraphs.

A1. A system for sampling material from cells, the system comprising: (a) a chip including an electrode array of sampling electrodes arranged along a surface of the chip, wherein a cell-receiving area is located adjacent the surface of the chip; (b) a tag array supported by the chip and aligned with the electrode array, the tag array being composed of tags, each tag of the tag array including an identifier that is unique to the tag within the tag array; and (c) a control circuit configured to apply an individually controllable voltage to each sampling electrode of the electrode array and measure an electrical property of the sampling electrode.

A2. The system of paragraph A1, wherein each tag of the tag array is a primer configured to hybridize to a poly(A) tail of RNA molecules.

A3. The system of paragraph A2, wherein the primer includes an oligo(dT) sequence of at least 3, 5, 7, or 10 consecutive deoxythymidine nucleotides at a 3'-end of the primer.

A4. The system of paragraph A2, wherein the primer includes a degenerate nucleotide sequence at a 3'-end of the primer.

A5. The system of paragraph A1, wherein copies of a capturing agent for nucleic acids or a protein are supported by the chip and aligned with each tag of the tag array, and wherein the capturing agent is not provided by the tag array, and wherein, optionally, the capturing agent is a specific binding partner (e.g., an antibody) for the protein.

A6. The system of paragraph A1, wherein the capturing agent includes a transposase.

A7. The system of paragraph A6, wherein the transposase is complexed with each tag of the tag array.

A8. The system of any of paragraphs A5 to A7, wherein the capturing agent includes a DNA-binding protein.

A9. The system of paragraph A8, wherein the DNA-binding protein binds double-stranded DNA.

A10. The system of any of paragraphs A1 to A9, wherein each tag of the tag array is connected to the chip.

A11. The system of paragraph A10, wherein each tag is attached to a porous layer located on a sampling electrode of the electrode array.

A12. The system of any of paragraphs A1 to A9, wherein each tag of the tag array is attached to a bead that is supported by the chip and located at least partially in a well defined by the chip, and wherein the bead is removable from the well.

A13. The system of any of paragraphs A1 to A12, wherein a well array of wells is formed in the surface of the chip, wherein each sampling electrode of the electrode array is located at the bottom of a different well of the well array, and wherein, optionally, each tag of the tag array is located in one of the wells of the well array.

A14. The system of paragraph A13, wherein each well of the well array has a diameter of less than 100, 50, 20, 10, or 5 micrometers.

A15. The system of paragraph A13 or A14, wherein each well of the well array has a depth of less than 100, 50, 20, 10, or 5 micrometers.

A16. The system of any of paragraphs A13 to A15, wherein the well array has an average center-to-center spacing between the wells that is at least twice an average diameter of the wells.

A17. The system of any of paragraphs A13 to A16, wherein the well array has an average center-to-center spacing between the wells that less than 20, 10, or 5 times an average diameter of the wells.

A18. The system of any of paragraphs A13 to A17, wherein the chip includes a dielectric layer, and wherein a side wall portion of each well is formed by the dielectric layer.

A19. The system of any of paragraphs A1 to A18, wherein the electrode array includes at least 1,000 electrodes.

A20. The system of any of paragraphs A1 to A19, wherein the electrode array is a planar array.

A21. The system of any of paragraphs A1 to A20, wherein the chip includes a substrate composed of a semiconductor, and wherein, optionally, the chip includes an integrated circuit, and wherein, optionally, the integrated circuit includes digital electronics.

A22. The system of any of paragraphs A1 to A21, further comprising one or more counter electrodes, wherein the control circuit is configured to apply the individual controllable voltage between the one or more counter electrodes and each sampling electrode of the electrode array.

A23. The system of paragraph A22, where the one or more counter electrodes are configured to face the electrode array.

A24. The system of paragraph A22 or A23, wherein the one or more counter electrodes are a single counter electrode.

A25. The system of any of paragraphs A22 to A24, wherein the cell-receiving area is located intermediate the electrode array and the one or more counter electrodes when the one or more counter electrodes are operatively positioned with respect to the electrode array, and/or wherein the one or more counter electrodes are configured to be movable with respect to the electrode array, to permit a tissue section to be placed in the cell-receiving array without interference from the one or more counter electrodes.

A26. The system of any of paragraphs A22 to A25, further comprising an electrolyte-receiving space between the cell-receiving area and the one or more counter electrodes when the one or more counter electrodes are operatively positioned with respect to the electrode array.

A27. The system of paragraph A26, further comprising an electrolyte gel configured to be disposed in the electrolyte-receiving space.

A28. The system of paragraph A27, wherein the electrolyte gel is a sheet.

A29. The system of any of paragraphs A1 to A28, wherein the chip includes one or more guard electrodes that are energizable by the control circuit and located along the surface of the chip intermediate sampling electrodes of the electrode array.

A30. The system of paragraph A29, further comprising one or more counter electrodes that are shared by the electrode array and the one or more guard electrodes.

A31. The system of paragraph A29 or A30, wherein the electrode array defines a plane, and wherein the one or more guard electrodes are offset from the plane.

A32 The system of any of paragraphs A1 to A31, wherein the chip forms at least a portion of a floor of a vessel that includes the cell-receiving area.

A33. The system of paragraph A32, further comprising a housing that forms side walls of the vessel.

A34. The system of paragraph A33, wherein the housing includes a cover for the vessel, wherein one or more counter electrodes for the electrode array form at least part of the cover.

A35. The system of paragraph A34, wherein the cover is movable with respect to a base of the housing.

A36. The system of any of paragraphs A1 to A31, wherein the cell-receiving area includes at least one channel disposed in fluid communication with a plurality of sampling electrodes of the electrode array.

A37. The system of any of paragraphs A1 to A36, wherein the control circuit is configured to apply a lysis voltage to each sampling electrode of the electrode array, to lyse a cell located in the cell-receiving area and aligned with the sampling electrode, if the electrical property measured for the sampling electrode meets one or more criteria.

A38. The system of paragraph A37, wherein the electrical property is electric current, and wherein the control circuit is configured to apply the lysis voltage to the sampling electrode if the electric current measured for the sampling electrode is below a threshold.

A39. The system of paragraph A38, wherein the control circuit is configured to apply a test voltage to each sampling electrode of the electrode array and measure an electric current produced by the test voltage, and wherein the lysis voltage is greater than the test voltage.

A40. The system of paragraph A39, wherein the lysis voltage includes a voltage spike that is at least twice the test voltage, and/or wherein the control circuit is configured to measure the electrical property again for the sampling electrode after the lysis voltage has been applied.

A41. The system of any of paragraphs A37 to A40, wherein the control circuit is configured to apply an electrophoresis voltage to the sampling electrode after applying the lysis voltage, to drive nucleic acids toward the sampling electrode for capture by a tag of the tag array (or for capture by a distinct capturing agent that is not provided by the tag array).

A42. The system of paragraph A41, wherein the control circuit is configured to apply a reverse voltage to the sampling electrode after application of the electrophoresis voltage, to remove nucleic acids not captured by the tag of the tag array or the distinct capturing agent.

A43. The system of any of paragraphs A37 to A42, wherein the control circuit is configured to generate data representing a percentage, number, and/or map of sampling electrodes of the electrode array at which capture of material (such as nucleic acids) from lysed cells is predicted to have occurred.

A44. The system of paragraph 43, wherein the control circuit is configured to generate the data based on (a) the electrical property measured for each sampling electrode, (b) which or how many sampling electrodes of the electrode array have received a lysis voltage, (c) which or how many sampling electrodes of the electrode array have received an electrophoresis voltage, or (d) any combination thereof.

A45. The system of paragraph A44, wherein the control circuit is configured to output the data as the control circuit continues to measure the electrical property for sampling electrodes of the electrode array at which capture of nucleic acids is predicted not to have occurred.

A46. The system of paragraph A44 or A45, wherein the control circuit is configured to control display of the data to a user.

A47. The system of any of paragraphs A1 to 46, wherein the surface is a top surface of the chip, and/or wherein the surface is planar, and/or wherein the surface forms a surface of the chip in which wells are formed and each sampling electrode is located at the bottom of a different one of the wells, and/or wherein each tag of the tag array is located in one of the wells of the well array.

A48. The method of any of paragraphs A1 to A47, further comprising any limitation or combination of limitations of paragraphs B1 to B19, C1, and D1 to D3.

B1. A method of sampling nucleic acid material from cells, the method comprising: (a) receiving a plurality of cells on a surface of a chip, the chip including an electrode array of sampling electrodes arranged along the surface; (b) measuring an electrical property for each sampling electrode of the electrode array; (c) applying a lysis voltage to the sampling electrode if the measured electrical property for the sampling electrode meets one or more criteria; and (d) applying an electrophoresis voltage to the sampling electrode, if the lysis voltage was applied to the sampling electrode, to drive nucleic acids, if any, that were released from one of the cells by applying the lysis voltage, toward the sampling electrode.

B2. The method of paragraph B1, wherein the chip includes a tag array of tags aligned with the electrode array, wherein each tag includes an identifier that is unique within the tag array, and wherein applying an electrophoresis voltage includes driving the nucleic acids, if any, to copies of a tag of the tag array that is aligned with the sampling electrode.

B3. The method of paragraph B2, wherein the tag is configured to hybridize with RNA molecules of the nucleic acids, to capture the RNA molecules.

B4. The method of any of paragraphs B1 to B3, wherein receiving a plurality of cells includes receiving a tissue section including the plurality of cells.

B5. The method of paragraph B4, further comprising receiving an electrolyte gel on the tissue section.

B6. The method of any of paragraphs B1 to B3, wherein receiving a plurality of cells including driving cells by fluid flow into a cell-receiving area located adjacent the surface of the chip.

B7. The method of any of paragraphs B1 to B6, wherein receiving a plurality of cells includes receiving a plurality of cells on a well array of wells aligned with the electrode array.

B8. The method of paragraph B7, wherein receiving a plurality of cells includes receiving a plurality of cells in respective alignment with each well of a plurality of wells of the well array.

B9. The method of any of paragraphs B1 to B8, wherein measuring an electrical property includes applying a test voltage to each sampling electrode of the electrode array and measuring an electric current produced by the test voltage.

B10. The method of paragraph B9, wherein applying a lysis voltage includes applying a lysis voltage to the sampling electrode if the electric current measured for the sampling electrode is below a threshold.

B11. The method of any of paragraphs B1 to B10, further comprising capturing nucleic acids with a capturing agent over each sampling electrode of a plurality of sampling electrodes of the electrode array.

B12. The method of paragraph B11, wherein capturing nucleic acids includes capturing RNA molecules of the nucleic acids by hybridization with the capturing agent.

B13. The method of any of paragraphs B1 to B12, wherein a tag array is aligned with the electrode array, wherein the tag array is composed of tags, wherein each tag has an identifier that is unique within the tag array, and wherein applying an electrophoresis voltage includes driving nucleic acids from the one cell, if any, that was lysed by the lysis potential, to a tag of the tag array that is aligned with the one cell.

B14. The method of paragraph B13, further comprising driving nucleic acids from two or more cells of the plurality of cells to a corresponding number of different tags of the tag array.

B15. The method of paragraph B14, further comprising covalently attaching each of the different tags to DNA from a different one of the two or more cells.

B16. The method of any paragraphs B1 to B15, further comprising outputting data representing a percentage, number, and/or map of sampling electrodes of the electrode array at which capture of nucleic acids from lysed cells is predicted to have occurred.

B17. The method of paragraph B16, wherein outputting data includes displaying the data.

B18. The method of paragraph B17, further comprising displaying the data as the control circuit continues to measure the electrical property for sampling electrodes of the electrode array at which a lysis voltage has not been applied.

B19. The method of any of paragraphs B1 to B18, further comprising preparing a library for sequencing, the library including nucleic acids captured over each sampling electrode of a plurality of sampling electrodes of the electrode array, or the library including fragments or complements of such captured nucleic acids.

B20. The method of any of paragraphs B1 to B19, further comprising any limitation or combination of limitations of paragraphs A1 to A47.

C1. A method of sampling nucleic acid material from cells, the method comprising: (a) receiving a tissue section on a surface of a chip, the chip including an electrode array of sampling electrodes arranged along the surface; (b) measuring an electrical property for each sampling electrode of the electrode array; (c) applying a lysis voltage to the sampling electrode if the measured electrical property for the sampling electrode meets one or more criteria; and (d) applying an electrophoresis voltage to the sampling electrode to drive nucleic acids, if any, that were released from a cell of the tissue section by the lysis voltage, to copies of a capturing agent for the nucleic acids.

D1. A method of sampling nucleic acid material from a tissue section, the method comprising: (a) selecting a chip including an electrode array of sampling electrodes arranged along a surface of the chip, the chip supporting a primer array aligned with the electrode array, the primer array being composed of primers, each primer being configured to hybridize to a poly(A) tail of RNA and including an identifier that is unique to the primer within the primer array; (b) receiving the tissue section on the surface of the chip; (c) measuring an electrical property for each sampling electrode of the electrode array; (d) applying a lysis voltage to the sampling electrode if the measured electrical property for the sampling electrode meets one or more criteria; and (e) capturing RNA molecules from the tissue section with each primer of a plurality of different primers of the primer array.

D2. The method of paragraph D1, the method further comprising applying an electrophoresis voltage to the sampling electrode to drive nucleic acids, if any, that were released from a cell of the tissue section by the lysis voltage, to a primer of the primer array that is aligned with the sampling electrode.

D3. The method of paragraph D1 or D2, further comprising any limitation or combination of limitations of paragraphs A1 to A48, B1 to B20, and C1.

The term "exemplary" as used in the present disclosure, means "illustrative" or "serving as an example." Similarly, the term "exemplify" means "to illustrate by giving an example." Neither term implies desirability or superiority.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for sampling material from cells, the system comprising:
   a chip including an electrode array of sampling electrodes arranged along a surface of the chip, wherein a cell-receiving area is located adjacent the surface of the chip, wherein a well array of wells is formed in the surface of the chip, wherein each sampling electrode of the electrode array is located at the bottom of a different well of the well array, and wherein each tag of the tag array is located in one of the wells of the well array;
   a tag array supported by the chip and aligned with the electrode array, the tag array being composed of tags, each tag of the tag array including an identifier that is unique to the tag within the tag array; and
   a control circuit configured to apply an individually controllable voltage to each sampling electrode of the electrode array and measure an electrical property of the sampling electrode, wherein the control circuit is configured to apply a lysis voltage to each sampling electrode of the electrode array, to lyse a cell located in the cell-receiving area and aligned with the sampling electrode, if the electrical property measured for the sampling electrode meets one or more predefined criteria.

2. The system of claim 1, wherein each tag of the tag array is a primer configured to hybridize to a poly(A) tail of RNA molecules.

3. The system of claim 2, wherein the primer includes a degenerate nucleotide sequence at a 3'-end of the primer.

4. The system of claim 1, wherein copies of a capturing agent for nucleic acids or a protein are supported by the chip and aligned with each tag of the tag array, and wherein the capturing agent is not provided by the tag array.

5. The system of claim 4, wherein the capturing agent is a specific binding partner for the protein.

6. The system of claim 4, wherein the capturing agent binds double-stranded DNA.

7. The system of claim 1, wherein the well array has an average center-to-center spacing between the wells that is at least twice an average diameter of the wells.

8. The system of claim 1, further comprising one or more counter electrodes, wherein the control circuit is configured to apply the individual controllable voltage between the one or more counter electrodes and each sampling electrode of the electrode array, and wherein the one or more counter electrodes are configured to be movable with respect to the electrode array, to permit a tissue section to be placed in the cell-receiving array without interference from the one or more counter electrodes.

9. The system of claim 1, wherein the chip forms at least a portion of a floor of a vessel that includes the cell-receiving area, further comprising a housing that forms side walls of the vessel, wherein the housing includes a cover for the vessel, wherein one or more counter electrodes for the electrode array form at least part of the cover, and wherein the cover is movable with respect to a base of the housing.

10. The system of claim 1, wherein the control circuit is configured to generate data representing a percentage, number, and/or map of sampling electrodes of the electrode array at which capture of material from lysed cells is predicted to have occurred.

11. The system of claim 1, wherein the control circuit is configured to apply an electrophoresis voltage to the sampling electrode after applying the lysis voltage, to drive nucleic acids toward the sampling electrode for capture by a tag of the tag array or by a distinct capturing agent that is not provided by the tag array.

12. The system of claim 11, wherein the control circuit is configured to apply a reverse voltage to the sampling electrode after application of the electrophoresis voltage, to remove nucleic acids not captured by the tag of the tag array or the distinct capturing agent.

13. The system of claim 1, wherein each tag of the tag array is attached to a bead that is supported by the chip and located at least partially in a well defined by the chip, and wherein the bead is removable from the well.

* * * * *